United States Patent
Sidar et al.

(10) Patent No.: US 10,123,684 B2
(45) Date of Patent: Nov. 13, 2018

(54) SYSTEM AND METHOD FOR PROCESSING VIDEO IMAGES GENERATED BY A MULTIPLE VIEWING ELEMENTS ENDOSCOPE

(71) Applicant: EndoChoice, Inc., Alpharetta, GA (US)

(72) Inventors: Itay Sidar, Haifa (IL); Tal Davidson, Yokneam Ilit (IL); Achia Kronman, Pardes Hana (IL)

(73) Assignee: EndoChoice, Inc., Alpharetta, GA (US)

( * ) Notice: Subject to any disclaimer, the term of this patent is extended or adjusted under 35 U.S.C. 154(b) by 392 days.

(21) Appl. No.: 14/967,771

(22) Filed: Dec. 14, 2015

(65) Prior Publication Data
US 2016/0174827 A1   Jun. 23, 2016

Related U.S. Application Data

(60) Provisional application No. 62/093,871, filed on Dec. 18, 2014.

(51) Int. Cl.
*A61B 1/04* (2006.01)
*H04N 3/14* (2006.01)
(Continued)

(52) U.S. Cl.
CPC .......... *A61B 1/042* (2013.01); *A61B 1/00009* (2013.01); *A61B 1/00177* (2013.01);
(Continued)

(58) Field of Classification Search
CPC .... A61B 1/00009; A61B 1/05; H04N 3/1568; H04N 5/243
(Continued)

(56) References Cited

U.S. PATENT DOCUMENTS 3,639,714 A   2/1972 Fujimoto
3,955,064 A   5/1976 Demetrio
(Continued)

FOREIGN PATENT DOCUMENTS

CA   2297986   3/1999
CA   2765559   12/2010
(Continued)

OTHER PUBLICATIONS

Office Action dated Jun. 30, 2016 for U.S. Appl. No. 13/655,120.
(Continued)

*Primary Examiner* — Jeremiah C Hallenbeck-Huber
(74) *Attorney, Agent, or Firm* — Bookoff McAndrews, PLLC

(57) ABSTRACT

An endoscope video processing system applies a blooming control feature to image frames of video data signals generated by viewing elements in the endoscope tip. A reduced digital gain is applied to a luminance (Y) component of the video data signal to generate an attenuated signal. An average luminance value of pixels neighboring a pixel of the attenuated signal is calculated and a function of the average luminance value is determined to generate a smoothly transitioning digital gain. The smoothly transitioning digital gain is conditioned using weights to generate a customizable digital gain, and the customizable digital gain is applied to the attenuated signal. This Local Blooming Control (LBC) facilitates a higher luminance digital gain in darker portions while maintaining a low or no luminance digital gain in brighter portions, within the same image frame.

19 Claims, 9 Drawing Sheets

(51) Int. Cl.
*H04N 5/235* (2006.01)
*H04N 5/243* (2006.01)
*H04N 5/372* (2011.01)
*H04N 5/374* (2011.01)
*A61B 1/00* (2006.01)
*A61B 1/045* (2006.01)
*A61B 1/05* (2006.01)
*H04N 5/355* (2011.01)
*H04N 5/359* (2011.01)
*H04N 5/225* (2006.01)

(52) U.S. Cl.
CPC .......... *A61B 1/00181* (2013.01); *A61B 1/045* (2013.01); *A61B 1/05* (2013.01); *H04N 3/1568* (2013.01); *H04N 5/2351* (2013.01); *H04N 5/243* (2013.01); *H04N 5/3591* (2013.01); *H04N 5/35536* (2013.01); *H04N 5/372* (2013.01); *H04N 5/374* (2013.01); *H04N 2005/2255* (2013.01)

(58) Field of Classification Search
USPC .......................................................... 348/65
See application file for complete search history.

(56) References Cited

U.S. PATENT DOCUMENTS

| | | |
|---|---|---|
| 4,027,697 A | 6/1977 | Bonney |
| 4,037,588 A | 7/1977 | Heckele |
| 4,084,401 A | 4/1978 | Belardi |
| 4,402,313 A | 9/1983 | Yabe |
| 4,461,282 A | 7/1984 | Ouchi |
| 4,494,549 A | 1/1985 | Namba |
| 4,532,918 A * | 8/1985 | Wheeler .............. A61B 1/0638 348/230.1 |
| 4,588,294 A | 5/1986 | Siegmund |
| 4,641,635 A | 2/1987 | Yabe |
| 4,727,859 A | 3/1988 | Lia |
| 4,764,001 A | 8/1988 | Yokota |
| 4,801,792 A | 1/1989 | Yamasita |
| 4,825,850 A | 5/1989 | Opie |
| 4,877,314 A | 10/1989 | Kanamori |
| 4,902,115 A | 2/1990 | Takahashi |
| 4,976,522 A | 12/1990 | Igarashi |
| 4,984,878 A | 1/1991 | Miyano |
| 5,007,406 A | 4/1991 | Takahashi |
| 5,014,685 A | 5/1991 | Takahashi |
| 5,193,525 A | 3/1993 | Silverstein |
| 5,224,929 A | 7/1993 | Remiszewski |
| 5,296,971 A | 3/1994 | Mori |
| 5,359,456 A | 10/1994 | Kikuchi |
| 5,395,329 A | 3/1995 | Fleischhacker |
| 5,447,148 A | 9/1995 | Oneda |
| 5,460,167 A | 10/1995 | Yabe |
| 5,464,007 A | 11/1995 | Krauter |
| 5,475,420 A | 12/1995 | Buchin |
| 5,489,256 A | 2/1996 | Adair |
| 5,518,501 A | 5/1996 | Oneda |
| 5,518,502 A | 5/1996 | Kaplan |
| 5,547,455 A | 8/1996 | McKenna |
| 5,547,457 A | 8/1996 | Tsuyuki |
| 5,575,755 A | 11/1996 | Krauter |
| 5,587,839 A | 12/1996 | Miyano |
| 5,630,782 A | 5/1997 | Adair |
| 5,630,798 A | 5/1997 | Beiser |
| 5,662,588 A | 9/1997 | Iida |
| 5,674,182 A | 10/1997 | Suzuki |
| 5,685,821 A | 11/1997 | Pike |
| 5,685,823 A | 11/1997 | Ito |
| 5,702,347 A | 12/1997 | Yabe |
| 5,707,344 A | 1/1998 | Nakazawa |
| 5,725,474 A | 3/1998 | Yasui |
| 5,725,476 A | 3/1998 | Yasui |
| 5,725,477 A | 3/1998 | Yasui |
| 5,725,478 A | 3/1998 | Saad |
| 5,777,797 A | 7/1998 | Miyano |
| 5,782,751 A | 7/1998 | Matsuno |
| 5,800,341 A | 9/1998 | McKenna |
| 5,810,715 A | 9/1998 | Moriyama |
| 5,810,717 A | 9/1998 | Maeda |
| 5,810,770 A | 9/1998 | Chin |
| 5,830,121 A | 11/1998 | Enomoto |
| 5,836,894 A | 11/1998 | Sarvazyan |
| 5,860,913 A | 1/1999 | Yamaya |
| 5,870,234 A | 2/1999 | Ebbesmeier |
| 5,916,148 A | 6/1999 | Tsuyuki |
| 5,940,126 A | 8/1999 | Kimura |
| 6,058,109 A | 5/2000 | Lechleider |
| 6,095,970 A | 8/2000 | Hidaka |
| 6,095,971 A | 8/2000 | Takahashi |
| 6,117,068 A | 9/2000 | Gourley |
| 6,181,481 B1 | 1/2001 | Yamamoto |
| 6,196,967 B1 | 3/2001 | Lim |
| 6,261,226 B1 | 7/2001 | McKenna |
| 6,277,064 B1 | 8/2001 | Yoon |
| 6,359,674 B1 | 3/2002 | Horiuchi |
| 6,375,610 B2 | 4/2002 | Verschuur |
| 6,402,738 B1 | 6/2002 | Ouchi |
| 6,419,626 B1 | 7/2002 | Yoon |
| 6,476,851 B1 | 11/2002 | Nakamura |
| 6,520,908 B1 | 2/2003 | Ikeda |
| 6,636,254 B1 | 10/2003 | Onishi |
| 6,638,214 B2 | 10/2003 | Akiba |
| 6,673,012 B2 | 1/2004 | Fujii |
| 6,690,337 B1 | 2/2004 | Mayer, III |
| 6,712,760 B2 | 3/2004 | Sano |
| 6,832,984 B2 | 12/2004 | Stelzer |
| 6,888,119 B2 | 5/2005 | Iizuka |
| 6,997,871 B2 | 2/2006 | Sonnenschein |
| 7,154,378 B1 | 12/2006 | Ertas |
| 7,435,218 B2 | 10/2008 | Krattiger |
| 7,621,869 B2 | 11/2009 | Ratnakar |
| 7,630,148 B1 | 12/2009 | Yang |
| 7,701,650 B2 | 4/2010 | Lin |
| 7,713,246 B2 | 5/2010 | Shia |
| 7,746,572 B2 | 6/2010 | Asami |
| 7,813,047 B2 | 10/2010 | Wang |
| 7,828,725 B2 | 11/2010 | Maruyama |
| 7,918,788 B2 | 4/2011 | Lin |
| 7,927,272 B2 | 4/2011 | Bayer |
| 7,967,745 B2 | 6/2011 | Gilad |
| 7,976,462 B2 | 7/2011 | Wright |
| 8,064,666 B2 | 11/2011 | Bayer |
| 8,182,422 B2 | 5/2012 | Bayer |
| 8,197,399 B2 | 6/2012 | Bayer |
| 8,235,887 B2 | 8/2012 | Bayer |
| 8,262,558 B2 | 9/2012 | Sato |
| 8,287,446 B2 | 10/2012 | Bayer |
| 8,289,381 B2 | 10/2012 | Bayer |
| 8,300,325 B2 | 10/2012 | Katahira |
| 8,310,530 B2 | 11/2012 | Bayer |
| 8,353,860 B2 | 1/2013 | Boulais |
| 8,447,132 B1 | 5/2013 | Galil |
| 8,449,457 B2 | 5/2013 | Aizenfeld |
| 8,460,182 B2 | 6/2013 | Ouyang |
| 8,585,584 B2 | 11/2013 | Ratnakar |
| 8,587,645 B2 | 11/2013 | Bayer |
| 8,672,836 B2 | 3/2014 | Higgins |
| 8,715,168 B2 | 5/2014 | Ratnakar |
| 8,797,392 B2 | 8/2014 | Bayer |
| 8,872,906 B2 | 10/2014 | Bayer |
| 8,926,502 B2 | 1/2015 | Levy |
| 9,044,185 B2 | 6/2015 | Bayer |
| 9,101,266 B2 | 8/2015 | Levi |
| 9,101,268 B2 | 8/2015 | Levy |
| 9,101,287 B2 | 8/2015 | Levy |
| 9,144,664 B2 | 9/2015 | Jacobsen |
| 9,289,110 B2 | 3/2016 | Woolford |
| 9,314,147 B2 | 4/2016 | Levy |
| 9,320,419 B2 | 4/2016 | Kirma |
| 2001/0036322 A1 | 11/2001 | Bloomfield |
| 2002/0017515 A1 | 2/2002 | Obata |
| 2002/0047897 A1 | 4/2002 | Sugimoto |

(56) References Cited

U.S. PATENT DOCUMENTS

| | | |
|---|---|---|
| 2002/0087047 A1 | 7/2002 | Remijan |
| 2002/0109771 A1 | 8/2002 | Ledbetter |
| 2002/0109774 A1 | 8/2002 | Meron |
| 2002/0161279 A1 | 10/2002 | Luloh |
| 2002/0161281 A1 | 10/2002 | Jaffe |
| 2002/0172498 A1 | 11/2002 | Esenyan |
| 2002/0183591 A1 | 12/2002 | Matsuura |
| 2003/0030918 A1 | 2/2003 | Murayama |
| 2003/0063398 A1 | 4/2003 | Abe |
| 2003/0076411 A1 | 4/2003 | Iida |
| 2003/0083552 A1 | 5/2003 | Remijan |
| 2003/0128893 A1 | 7/2003 | Castorina |
| 2003/0139650 A1 | 7/2003 | Homma |
| 2003/0153897 A1 | 8/2003 | Russo |
| 2003/0158503 A1 | 8/2003 | Matsumoto |
| 2003/0163029 A1 | 8/2003 | Sonnenschein |
| 2004/0015054 A1 | 1/2004 | Hino |
| 2004/0046865 A1 | 3/2004 | Ueno |
| 2004/0061780 A1 | 4/2004 | Huffman |
| 2004/0064019 A1 | 4/2004 | Chang |
| 2004/0077927 A1 | 4/2004 | Ouchi |
| 2004/0106850 A1 | 6/2004 | Yamaya |
| 2004/0133072 A1 | 7/2004 | Kennedy |
| 2004/0138532 A1 | 7/2004 | Glukhovsky |
| 2004/0158129 A1 | 8/2004 | Okada |
| 2004/0160682 A1 | 8/2004 | Miyano |
| 2004/0190159 A1 | 9/2004 | Hasegawa |
| 2004/0249247 A1 | 12/2004 | Iddan |
| 2004/0260151 A1 | 12/2004 | Akiba |
| 2005/0018042 A1 | 1/2005 | Rovegno |
| 2005/0020876 A1 | 1/2005 | Shioda |
| 2005/0038317 A1 | 2/2005 | Ratnakar |
| 2005/0047134 A1 | 3/2005 | Mueller |
| 2005/0057687 A1 | 3/2005 | Irani |
| 2005/0090709 A1 | 4/2005 | Okada |
| 2005/0096501 A1 | 5/2005 | Stelzer |
| 2005/0119527 A1 | 6/2005 | Banik |
| 2005/0124858 A1 | 6/2005 | Matsuzawa |
| 2005/0222499 A1 | 10/2005 | Banik |
| 2005/0234296 A1 | 10/2005 | Saadat |
| 2005/0234347 A1 | 10/2005 | Yamataka |
| 2005/0251127 A1 | 11/2005 | Brosch |
| 2005/0272975 A1 | 12/2005 | McWeeney |
| 2005/0277808 A1 | 12/2005 | Sonnenschein |
| 2005/0283048 A1 | 12/2005 | Gill |
| 2006/0004257 A1 | 1/2006 | Gilad |
| 2006/0047184 A1 | 3/2006 | Banik |
| 2006/0063976 A1 | 3/2006 | Aizenfeld |
| 2006/0069314 A1 | 3/2006 | Farr |
| 2006/0111613 A1 | 5/2006 | Boutillette |
| 2006/0114986 A1 | 6/2006 | Knapp |
| 2006/0149129 A1 | 7/2006 | Watts |
| 2006/0171693 A1 | 8/2006 | Todd |
| 2006/0173245 A1 | 8/2006 | Todd |
| 2006/0183975 A1 | 8/2006 | Saadat |
| 2006/0184037 A1 | 8/2006 | Ince |
| 2006/0189845 A1 | 8/2006 | Maahs |
| 2006/0215406 A1 | 9/2006 | Thrailkill |
| 2006/0235306 A1 | 10/2006 | Cotter |
| 2006/0252994 A1 | 11/2006 | Ratnakar |
| 2006/0264704 A1 | 11/2006 | Fujimori |
| 2006/0293556 A1 | 12/2006 | Garner |
| 2007/0015989 A1 | 1/2007 | Desai |
| 2007/0046786 A1* | 3/2007 | Tokuyama ............. H04N 5/357 348/222.1 |
| 2007/0049803 A1 | 3/2007 | Moriyama |
| 2007/0055100 A1 | 3/2007 | Kato |
| 2007/0079029 A1 | 4/2007 | Carlson |
| 2007/0088193 A1 | 4/2007 | Omori |
| 2007/0100206 A1 | 5/2007 | Lin |
| 2007/0106119 A1 | 5/2007 | Hirata |
| 2007/0118015 A1 | 5/2007 | Wendlandt |
| 2007/0142711 A1 | 6/2007 | Bayer |
| 2007/0162095 A1 | 7/2007 | Kimmel |
| 2007/0167681 A1 | 7/2007 | Gill |
| 2007/0177008 A1 | 8/2007 | Bayer |
| 2007/0177009 A1 | 8/2007 | Bayer |
| 2007/0185384 A1 | 8/2007 | Bayer |
| 2007/0188427 A1 | 8/2007 | Lys |
| 2007/0197875 A1 | 8/2007 | Osaka |
| 2007/0203396 A1 | 8/2007 | McCutcheon |
| 2007/0206945 A1 | 9/2007 | Delorme |
| 2007/0213591 A1 | 9/2007 | Aizenfeld |
| 2007/0229656 A1 | 10/2007 | Khait |
| 2007/0241895 A1 | 10/2007 | Morgan |
| 2007/0244353 A1 | 10/2007 | Larsen |
| 2007/0244354 A1 | 10/2007 | Bayer |
| 2007/0247867 A1 | 10/2007 | Hunter |
| 2007/0249907 A1 | 10/2007 | Boulais |
| 2007/0265492 A1 | 11/2007 | Sonnenschein |
| 2007/0270642 A1 | 11/2007 | Bayer |
| 2007/0279486 A1 | 12/2007 | Bayer |
| 2007/0286764 A1 | 12/2007 | Noguchi |
| 2007/0293720 A1 | 12/2007 | Bayer |
| 2008/0009673 A1 | 1/2008 | Khachi |
| 2008/0021274 A1 | 1/2008 | Bayer |
| 2008/0025413 A1 | 1/2008 | Apostolopoulos |
| 2008/0036864 A1 | 2/2008 | McCubbrey |
| 2008/0045797 A1 | 2/2008 | Yasushi |
| 2008/0058601 A1 | 3/2008 | Fujimori |
| 2008/0071290 A1 | 3/2008 | Larkin |
| 2008/0091065 A1 | 4/2008 | Oshima |
| 2008/0130108 A1 | 6/2008 | Bayer |
| 2008/0151070 A1 | 6/2008 | Shiozawa |
| 2008/0161646 A1 | 7/2008 | Gomez |
| 2008/0163652 A1 | 7/2008 | Shatskin |
| 2008/0167529 A1 | 7/2008 | Otawara |
| 2008/0177139 A1 | 7/2008 | Courtney |
| 2008/0183034 A1 | 7/2008 | Henkin |
| 2008/0183043 A1 | 7/2008 | Spinnler |
| 2008/0221388 A1 | 7/2008 | Courtney |
| 2008/0246771 A1 | 10/2008 | ONeal |
| 2008/0253686 A1 | 10/2008 | Bayer |
| 2008/0262312 A1 | 10/2008 | Carroll |
| 2008/0275298 A1 | 11/2008 | Ratnakar |
| 2008/0291296 A1* | 11/2008 | Oike ................... H04N 5/3591 348/234 |
| 2008/0303898 A1 | 12/2008 | Nishimura |
| 2009/0005643 A1 | 1/2009 | Smith |
| 2009/0023998 A1 | 1/2009 | Ratnakar |
| 2009/0030275 A1 | 1/2009 | Nicolaou |
| 2009/0052769 A1* | 2/2009 | Kang ..................... H04N 9/045 382/162 |
| 2009/0054790 A1 | 2/2009 | Czaniera |
| 2009/0062615 A1 | 3/2009 | Yamaya |
| 2009/0076327 A1 | 3/2009 | Ohki |
| 2009/0082624 A1 | 3/2009 | Joko |
| 2009/0086017 A1 | 4/2009 | Miyano |
| 2009/0127436 A1* | 5/2009 | Johnson ............ H01L 27/14656 250/208.1 |
| 2009/0135245 A1 | 5/2009 | Luo |
| 2009/0137875 A1 | 5/2009 | Kitagawa |
| 2009/0143647 A1 | 6/2009 | Banju |
| 2009/0147076 A1 | 6/2009 | Ertas |
| 2009/0182917 A1 | 7/2009 | Kim |
| 2009/0213211 A1 | 8/2009 | Bayer |
| 2009/0216084 A1 | 8/2009 | Yamane |
| 2009/0225159 A1 | 9/2009 | Schneider |
| 2009/0231419 A1 | 9/2009 | Bayer |
| 2009/0234183 A1 | 9/2009 | Abe |
| 2009/0253966 A1 | 10/2009 | Ichimura |
| 2009/0287188 A1 | 11/2009 | Golden |
| 2009/0287192 A1 | 11/2009 | Vivenzio |
| 2009/0299144 A1 | 12/2009 | Shigemori |
| 2010/0010309 A1 | 1/2010 | Kitagawa |
| 2010/0016673 A1 | 1/2010 | Bandy |
| 2010/0053312 A1 | 3/2010 | Watanabe |
| 2010/0069713 A1 | 3/2010 | Endo |
| 2010/0073470 A1 | 3/2010 | Takasaki |
| 2010/0073948 A1 | 3/2010 | Stein |
| 2010/0076268 A1 | 3/2010 | Takasugi |
| 2010/0123950 A1 | 5/2010 | Fujiwara |
| 2010/0130822 A1 | 5/2010 | Katayama |
| 2010/0141763 A1 | 6/2010 | Itoh |

(56) References Cited

U.S. PATENT DOCUMENTS

| | | | |
|---|---|---|---|
| 2010/0149340 A1* | 6/2010 | Marks | H04N 5/217 348/169 |
| 2010/0160729 A1 | 6/2010 | Smith | |
| 2010/0174144 A1 | 7/2010 | Hsu | |
| 2010/0231702 A1 | 9/2010 | Tsujimura | |
| 2010/0245653 A1 | 9/2010 | Bodor | |
| 2010/0249513 A1 | 9/2010 | Tydlaska | |
| 2010/0280322 A1 | 11/2010 | Mizuyoshi | |
| 2010/0296178 A1 | 11/2010 | Genet | |
| 2010/0326703 A1 | 12/2010 | Gilad | |
| 2011/0004058 A1 | 1/2011 | Oneda | |
| 2011/0004059 A1 | 1/2011 | Arneson | |
| 2011/0034769 A1 | 2/2011 | Adair | |
| 2011/0063427 A1 | 3/2011 | Fengler | |
| 2011/0084835 A1 | 4/2011 | Whitehouse | |
| 2011/0140003 A1 | 6/2011 | Beck | |
| 2011/0160530 A1 | 6/2011 | Ratnakar | |
| 2011/0160535 A1 | 6/2011 | Bayer | |
| 2011/0169931 A1 | 7/2011 | Pascal | |
| 2011/0184243 A1 | 7/2011 | Wright | |
| 2011/0211267 A1 | 9/2011 | Takato | |
| 2011/0254937 A1 | 10/2011 | Yoshino | |
| 2011/0263938 A1 | 10/2011 | Levy | |
| 2011/0282144 A1 | 11/2011 | Gettman | |
| 2011/0292258 A1 | 12/2011 | Adler | |
| 2012/0040305 A1 | 2/2012 | Karazivan | |
| 2012/0050606 A1 | 3/2012 | Debevec | |
| 2012/0053407 A1 | 3/2012 | Levy | |
| 2012/0057251 A1 | 3/2012 | Takato | |
| 2012/0065468 A1 | 3/2012 | Levy | |
| 2012/0076425 A1 | 3/2012 | Brandt | |
| 2012/0162402 A1 | 6/2012 | Amano | |
| 2012/0200683 A1 | 8/2012 | Oshima | |
| 2012/0209071 A1 | 8/2012 | Bayer | |
| 2012/0209289 A1 | 8/2012 | Duque | |
| 2012/0212630 A1 | 8/2012 | Pryor | |
| 2012/0220832 A1 | 8/2012 | Nakade | |
| 2012/0224026 A1 | 9/2012 | Bayer | |
| 2012/0229615 A1 | 9/2012 | Kirma | |
| 2012/0232340 A1 | 9/2012 | Levy | |
| 2012/0232343 A1 | 9/2012 | Levy | |
| 2012/0253121 A1 | 10/2012 | Kitano | |
| 2012/0277535 A1 | 11/2012 | Hoshino | |
| 2012/0281536 A1 | 11/2012 | Gell | |
| 2012/0289858 A1 | 11/2012 | Ouyang | |
| 2012/0300999 A1 | 11/2012 | Bayer | |
| 2013/0033616 A1* | 2/2013 | Kaizu | H04N 5/35554 348/222.1 |
| 2013/0053646 A1 | 2/2013 | Yamamoto | |
| 2013/0057724 A1 | 3/2013 | Miyahara | |
| 2013/0060086 A1 | 3/2013 | Talbert | |
| 2013/0066297 A1 | 3/2013 | Shtul | |
| 2013/0070128 A1* | 3/2013 | Suzuki | H04N 5/367 348/246 |
| 2013/0077257 A1 | 3/2013 | Tsai | |
| 2013/0085329 A1 | 4/2013 | Morrissette | |
| 2013/0109916 A1 | 5/2013 | Levy | |
| 2013/0116506 A1 | 5/2013 | Bayer | |
| 2013/0131447 A1 | 5/2013 | Benning | |
| 2013/0137930 A1 | 5/2013 | Menabde | |
| 2013/0141557 A1 | 6/2013 | Kawata | |
| 2013/0150671 A1 | 6/2013 | Levy | |
| 2013/0158344 A1 | 6/2013 | Taniguchi | |
| 2013/0169843 A1 | 7/2013 | Ono | |
| 2013/0172670 A1 | 7/2013 | Levy | |
| 2013/0172676 A1 | 7/2013 | Levy | |
| 2013/0197309 A1 | 8/2013 | Sakata | |
| 2013/0197556 A1 | 8/2013 | Shelton | |
| 2013/0222640 A1 | 8/2013 | Baek | |
| 2013/0253268 A1 | 9/2013 | Okada | |
| 2013/0264465 A1 | 10/2013 | Dai | |
| 2013/0267778 A1 | 10/2013 | Rehe | |
| 2013/0271588 A1 | 10/2013 | Kirma | |
| 2013/0274551 A1 | 10/2013 | Kirma | |
| 2013/0281925 A1 | 10/2013 | Benscoter | |
| 2013/0296649 A1 | 11/2013 | Kirma | |
| 2013/0303979 A1 | 11/2013 | Stieglitz | |
| 2013/0317295 A1 | 11/2013 | Morse | |
| 2014/0018624 A1 | 1/2014 | Bayer | |
| 2014/0031627 A1 | 1/2014 | Jacobs | |
| 2014/0046136 A1 | 2/2014 | Bayer | |
| 2014/0107418 A1 | 4/2014 | Ratnakar | |
| 2014/0148644 A1 | 5/2014 | Levi | |
| 2014/0184766 A1 | 7/2014 | Amling | |
| 2014/0213850 A1 | 7/2014 | Levy | |
| 2014/0225998 A1 | 8/2014 | Dai | |
| 2014/0247378 A1* | 9/2014 | Sharma | H04N 5/35536 348/280 |
| 2014/0276207 A1 | 9/2014 | Ouyang | |
| 2014/0296628 A1 | 10/2014 | Kirma | |
| 2014/0296643 A1 | 10/2014 | Levy | |
| 2014/0296866 A1 | 10/2014 | Salman | |
| 2014/0298932 A1 | 10/2014 | Okamoto | |
| 2014/0309495 A1 | 10/2014 | Kirma | |
| 2014/0316198 A1 | 10/2014 | Krivopisk | |
| 2014/0316204 A1 | 10/2014 | Ofir | |
| 2014/0320617 A1 | 10/2014 | Parks | |
| 2014/0333742 A1 | 11/2014 | Salman | |
| 2014/0333743 A1 | 11/2014 | Gilreath | |
| 2014/0336459 A1 | 11/2014 | Bayer | |
| 2014/0343358 A1 | 11/2014 | Hameed | |
| 2014/0343361 A1 | 11/2014 | Salman | |
| 2014/0343489 A1 | 11/2014 | Lang | |
| 2014/0364691 A1 | 12/2014 | Krivopisk | |
| 2014/0364692 A1 | 12/2014 | Salman | |
| 2014/0364694 A1 | 12/2014 | Avron | |
| 2015/0005581 A1 | 1/2015 | Salman | |
| 2015/0045614 A1 | 2/2015 | Krivopisk | |
| 2015/0057500 A1 | 2/2015 | Salman | |
| 2015/0094536 A1 | 4/2015 | Wieth | |
| 2015/0099925 A1 | 4/2015 | Davidson | |
| 2015/0099926 A1 | 4/2015 | Davidson | |
| 2015/0105618 A1 | 4/2015 | Levy | |
| 2015/0164308 A1 | 6/2015 | Ratnakar | |
| 2015/0182105 A1 | 7/2015 | Salman | |
| 2015/0196190 A1 | 7/2015 | Levy | |
| 2015/0201827 A1 | 7/2015 | Sidar | |
| 2015/0208900 A1 | 7/2015 | Vidas | |
| 2015/0208909 A1 | 7/2015 | Davidson | |
| 2015/0223676 A1 | 8/2015 | Bayer | |
| 2015/0230698 A1 | 8/2015 | Cline | |
| 2015/0305601 A1 | 10/2015 | Levi | |
| 2015/0313445 A1 | 11/2015 | Davidson | |
| 2015/0313450 A1 | 11/2015 | Wieth | |
| 2015/0313451 A1 | 11/2015 | Salman | |
| 2015/0320300 A1 | 11/2015 | Gershov | |
| 2015/0342446 A1 | 12/2015 | Levy | |
| 2015/0359415 A1 | 12/2015 | Lang | |
| 2015/0374206 A1 | 12/2015 | Shimony | |
| 2016/0015257 A1 | 1/2016 | Levy | |
| 2016/0015258 A1 | 1/2016 | Levin | |
| 2016/0058268 A1 | 3/2016 | Salman | |

FOREIGN PATENT DOCUMENTS

| | | |
|---|---|---|
| CA | 2812097 | 3/2012 |
| CA | 2798716 | 6/2013 |
| CA | 2798729 | 6/2013 |
| CN | 103348470 | 10/2013 |
| CN | 103403605 | 11/2013 |
| CN | 103491854 | 1/2014 |
| CN | 103702604 | 4/2014 |
| CN | 103732120 | 4/2014 |
| CN | 104717916 | 6/2015 |
| CN | 105246393 | 1/2016 |
| CN | 105324065 | 2/2016 |
| CN | 105324066 | 2/2016 |
| CN | 105338875 | 2/2016 |
| CN | 105358042 | 2/2016 |
| CN | 105358043 | 2/2016 |
| CN | 105377106 | 3/2016 |
| CN | 105407788 | 3/2016 |
| DE | 202010016900 | 5/2011 |
| EP | 1690497 | 8/2006 |

(56) References Cited

FOREIGN PATENT DOCUMENTS

| | | |
|---|---|---|
| EP | 1835844 | 9/2007 |
| EP | 1968425 | 9/2008 |
| EP | 1986541 | 11/2008 |
| EP | 1988813 | 11/2008 |
| EP | 2023794 | 2/2009 |
| EP | 2023795 | 2/2009 |
| EP | 2190341 | 6/2010 |
| EP | 2211683 | 8/2010 |
| EP | 2457492 | 5/2012 |
| EP | 2457493 | 5/2012 |
| EP | 1988812 | 11/2012 |
| EP | 2520218 | 11/2012 |
| EP | 2604175 | 6/2013 |
| EP | 2618718 | 7/2013 |
| EP | 2635932 | 9/2013 |
| EP | 2648602 | 10/2013 |
| EP | 2649648 | 10/2013 |
| EP | 2672878 | 12/2013 |
| EP | 2736400 | 6/2014 |
| EP | 2744390 | 6/2014 |
| EP | 2442706 | 11/2014 |
| EP | 2865322 | 4/2015 |
| EP | 2908714 | 8/2015 |
| EP | 2979123 | 2/2016 |
| EP | 2991537 | 3/2016 |
| EP | 2994032 | 3/2016 |
| EP | 2994033 | 3/2016 |
| EP | 2994034 | 3/2016 |
| EP | 2996536 | 3/2016 |
| EP | 2996541 | 3/2016 |
| EP | 2996542 | 3/2016 |
| EP | 2996621 | 3/2016 |
| GB | 12196628 | 3/2015 |
| JP | H1043129 | 2/1998 |
| JP | H10239740 | 9/1998 |
| JP | 11137512 | 5/1999 |
| JP | 2005253543 | 9/2005 |
| JP | 2006025888 | 2/2006 |
| JP | 2006068109 | 3/2006 |
| JP | 2010178766 A | 8/2010 |
| JP | 2012135432 | 7/2012 |
| JP | 2013116277 A2 | 6/2013 |
| JP | 2013123647 | 6/2013 |
| JP | 2013123648 | 6/2013 |
| JP | 2013208459 | 10/2013 |
| JP | 2013215582 | 10/2013 |
| JP | 2013230383 | 11/2013 |
| JP | 2013542467 | 11/2013 |
| JP | 2013544617 | 12/2013 |
| JP | 2014524303 | 9/2014 |
| JP | 2014524819 | 9/2014 |
| JP | 2015533300 | 11/2015 |
| WO | 2006073676 | 7/2006 |
| WO | 2006073725 | 7/2006 |
| WO | 2007070644 | 6/2007 |
| WO | 2007092533 | 8/2007 |
| WO | 2007092636 | 8/2007 |
| WO | 2007087421 | 11/2007 |
| WO | 2007136859 | 11/2007 |
| WO | 2007136879 | 11/2007 |
| WO | 2008015164 | 2/2008 |
| WO | 2009014895 | 1/2009 |
| WO | 2009015396 | 1/2009 |
| WO | 2009049322 | 4/2009 |
| WO | 2009049324 | 4/2009 |
| WO | 2009062179 | 5/2009 |
| WO | 2010146587 | 12/2010 |
| WO | 2012038958 | 3/2012 |
| WO | 2012056453 | 5/2012 |
| WO | 2012075153 A2 | 6/2012 |
| WO | 2012077116 | 6/2012 |
| WO | 2012077117 | 6/2012 |
| WO | 2012096102 | 7/2012 |
| WO | 2012120507 | 9/2012 |
| WO | 2013014673 | 1/2013 |
| WO | 2013024476 | 2/2013 |
| WO | 2014061023 | 4/2014 |
| WO | 2014160983 | 10/2014 |
| WO | 2014179236 | 11/2014 |
| WO | 2014182723 | 11/2014 |
| WO | 2014182728 | 11/2014 |
| WO | 2014183012 | 11/2014 |
| WO | 2014186230 | 11/2014 |
| WO | 2014186519 | 11/2014 |
| WO | 2014186521 | 11/2014 |
| WO | 2014186525 | 11/2014 |
| WO | 2014186775 | 11/2014 |
| WO | 2014210516 | 12/2014 |
| WO | 2015002847 | 1/2015 |
| WO | 2015047631 | 4/2015 |
| WO | 2015050829 | 4/2015 |
| WO | 2015084442 | 6/2015 |
| WO | 2015095481 | 6/2015 |
| WO | 2015112747 | 7/2015 |
| WO | 2015112899 | 7/2015 |
| WO | 2015134060 | 9/2015 |
| WO | 2015168066 | 11/2015 |
| WO | 2015168664 | 11/2015 |
| WO | 2015171732 | 11/2015 |
| WO | 2015175246 | 11/2015 |
| WO | 2016014581 | 1/2016 |
| WO | 2016033403 | 3/2016 |

OTHER PUBLICATIONS

Office Action dated Jun. 28, 2016 for U.S. Appl. No. 14/278,293.
Office Action dated Jul. 1, 2016 for U.S. Appl. No. 14/229,699.
Office Action dated Jul. 15, 2016 for U.S. Appl. No. 14/273,923.
Notice of Allowance dated Jul. 15, 2016 for U.S. Appl. No. 14/274,323.
Office Action dated Jul. 22, 2016 for U.S. Appl. No. 14/549,265.
Sherman L.M., Plastics That Conduct Hear, Plastics Technology, Jun. 2001—article obtained online from http://www.otonline.com/articles/plastics-that-conduct-heat.
Office Action dated Aug. 11, 2016 for U.S. Appl. No. 14/318,249.
Office Action dated Apr. 28, 2016 for U.S. Appl. No. 13/992,014.
Notice of Allowance dated Aug. 26, 2016 for U.S. Appl. No. 13/212,627.
Office Action dated Sep. 2, 2016 for U.S. Appl. No. 14/278,338.
Office Action dated Sep. 16, 2016 for U.S. Appl. No. 13/992,014.
Notice of Allowance dated Oct. 12, 2016 for U.S. Appl. No. 13/119,032.
Office Action dated Oct. 7, 2016 for U.S. Appl. No. 13/713,449.
Office Action dated Oct. 5, 2016 for U.S. Appl. No. 14/271,270.
Notice of Allowance dated Oct. 13, 2016 for U.S. Appl. No. 14/273,923.
Notice of Allowance dated Nov. 9, 2016 for U.S. Appl. No. 13/557,114.
Office Action dated Dec. 1, 2016 for U.S. Appl. No. 14/278,293.
Office Action dated Dec. 9, 2016 for U.S. Appl. No. 14/549,265.
Office Action dated Dec. 16, 2016 for U.S. Appl. No. 14/263,896.
Notice of Allowance dated Dec. 28, 2016 for U.S. Appl. No. 14/229,699.
Notice of Allowance dated Dec. 27, 2016 for U.S. Appl. No. 14/317,863.
Office Action dated Dec. 27, 2016 for U.S. Appl. No. 14/603,137.
Office Action dated Dec. 29, 2016 for U.S. Appl. No. 15/077,513.
Office Action dated Dec. 30, 2016 for U.S. Appl. No. 14/457,268.
Office Action dated Jan. 17, 2017 for U.S. Appl. No. 14/318,189.
Notice of Allowance dated Jan. 31, 2017 for U.S. Appl. No. 14/271,234.
Office Action dated Feb. 2, 2017 for U.S. Appl. No. 14/278,338.
Office Action dated Feb. 9, 2017 for U.S. Appl. No. 14/746,986.
Office Action dated Feb. 6, 2017 for U.S. Appl. No. 14/751,835.
Office Action dated Feb. 14, 2017 for U.S. Appl. No. 14/271,270.
Office Action dated Feb. 23, 2017 for U.S. Appl. No. 14/318,249.
Office Action dated Mar. 9, 2017 for U.S. Appl. No. 14/791,316.
Office Action dated Mar. 21, 2017 for U.S. Appl. No. 13/992,014.
Office Action dated Mar. 20, 2017 for U.S. Appl. No. 14/278,293.

(56) References Cited

OTHER PUBLICATIONS

Notice of Allowance dated Mar. 21, 2017 for U.S. Appl. No. 14/549,265.
Office Action dated Mar. 22, 2017 for U.S. Appl. No. 14/705,355.
Office Action dated Mar. 24, 2017 for U.S. Appl. No. 14/838,509.
Notice of Allowance dated Apr. 12, 2017 for U.S. Appl. No. 14/603,137.
Notice of Allowance dated Apr. 18, 2017 for U.S. Appl. No. 13/713,449.
Office Action dated Apr. 19, 2017 for U.S. Appl. No. 14/988,551.
Notice of Allowability dated Apr. 21, 2017 for U.S. Appl. No. 14/549,265.
Office Action dated May 11, 2017 for U.S. Appl. No. 14/278,293.
Office Action dated May 10, 2017 for U.S. Appl. No. 14/988,551.
Office Action dated May 5, 2017 for U.S. Appl. No. 15/077,513.
Notice of Allowance dated May 15, 2017 for U.S. Appl. No. 14/271,270.
Office Action dated May 15, 2017 for U.S. Appl. No. 14/278,293.
Office Action dated May 18, 2017 for U.S. Appl. No. 14/278,338.
Notice of Allowance dated May 16, 2017 for U.S. Appl. No. 14/746,386.
Office Action dated May 23, 2017 for U.S. Appl. No. 13/655,120.
International Search Report for PCT/US2015/6548, dated Feb. 26, 2016.
International Search Report for PCT/US14/37004, dated Sep. 25, 2014.
International Search Report for PCT/US2014/037526, dated Oct. 16, 2014.
International Search Report for PCT/US14/38094, dated Nov. 6, 2014.
International Search Report for PCT/US2015/012751, dated Jun. 26, 2015.
International Search Report for PCT/US2014/58143, dated Jan. 21, 2015.
International Search Report for PCT/US2014/071085, dated Mar. 27, 2015.
International Search Report for PCT/US2015/027902, dated Jul. 23, 2015.
International Search Report for PCT/US2015/012506, dated Dec. 11, 2015.
International Search Report for PCT/US2015/29421, dated Aug. 7, 2015.
International Search Report for PCT/US2015/28962, dated Jul. 28, 2015.
International Search Report for PCT/US2015/47334, dated Dec. 28, 2015.
International Search Report for PCT/US2015/41396, dated Sep. 29, 2015.
International Search Report for PCT/US2015/66486, dated Dec. 17, 2015.
Office Action date Feb. 26, 2016 for U.S. Appl. No. 14/274,323.
Office Action dated Feb. 4, 2016 for U.S. Appl. No. 14/271,234.
Corrected Notice of Allowance dated Apr. 13, 2016 for U.S. Appl. No. 13/680,646.
Notice of Allowance dated Mar. 28, 2016 for U.S. Appl. No. 13/413,059.
Notice of Allowance dated Mar. 29, 2016 for U.S. Appl. No. 13/680,646.
Office Action dated Mar. 23, 2016 for U.S. Appl. No. 13/713,449.
Office Action dated Mar. 24, 2016 for U.S. Appl. No. 13/212,627.
Office Action dated Mar. 28, 2016 for U.S. Appl. No. 13/119,032.
Office Action dated May 25, 2016 for U.S. Appl. No. 14/271,234.
Office Action dated May 5, 2016 for U.S. Appl. No. 14/278,338.
Office Action dated May 6, 2016 for U.S. Appl. No. 14/263,896.
Notice of Allowance dated May 25, 2017 for U.S. Appl. No. 14/318,189.
Office Action dated May 23, 2017 for U.S. Appl. No. 14/500,975.

* cited by examiner

SYSTEM AND METHOD FOR PROCESSING VIDEO IMAGES GENERATED BY A MULTIPLE VIEWING ELEMENTS ENDOSCOPE

CROSS-REFERENCE

The present specification relies on U.S. Patent Provisional Application No. 62/093,871, entitled "System and Method for Processing Video Images Generated By A Multiple Viewing Elements Endoscope", and filed on Dec. 18, 2014, for priority. The '871 application is incorporated herein by reference.

FIELD

The present specification generally relates to a multiple viewing elements endoscope, and more particularly to controlling bloomed or saturated areas of video images generated by the viewing elements of the endoscope.

BACKGROUND

Endoscopes, such as colonoscopes, that are currently being used, typically have multiple viewing elements, such as cameras, that correspondingly include Charge Coupled Device (CCD) or CMOS image sensors to generate video feeds. CCD as well as CMOS image sensors are fraught with problems, such as saturation and blooming, that affect both their quantitative and qualitative imaging characteristics. For example, if each individual pixel can be thought of as a well of electrons, then saturation refers to the condition where the well becomes filled. The amount of charge that can be accumulated in a single pixel is determined largely by its area. However, due to the nature of the potential well, which holds charge within a pixel, there is less probability of trapping an electron within a well that is approaching saturation. Therefore, as a well approaches its limit, the linear relationship between light intensity and signal degrades. As a result, the apparent responsivity of a saturated pixel drops.

At saturation, pixels lose their ability to accommodate additional charge. This additional charge then spreads into neighboring pixels, causing them to either report erroneous values or also saturate. This spread of charge to adjacent pixels is known as blooming and appears as a white streak or blob in the image. The occurrence of blooming, in video images generated by a multi-viewing elements endoscope, results in loss of details in portions of the video image and is a serious cause of concern for a physician performing an endoscopic procedure.

Accordingly, there is need in the art for processing the video feeds generated by a plurality of viewing elements of an endoscopic tip such that saturation is minimized and/or the occurrence of blooming is effectively controlled in the video feeds.

SUMMARY

The following embodiments and aspects thereof are described and illustrated in conjunction with systems, tools and methods, which are meant to be exemplary and illustrative, not limiting in scope.

The present specification discloses an endoscope video processing system for controlling blooming in an image frame of a video data signal generated by a viewing element of an endoscope, to facilitate an increased luminance digital gain in regions of a first brightness within the image frame while maintaining a decreased luminance digital gain in regions of a second brightness, wherein the first brightness is lower than the second brightness, said video processing system comprising: a processor; a memory; a digital signal processor for applying a reduced digital gain to a luminance (Y) component of the video data signal to generate an attenuated signal, wherein the reduced digital gain is defined by a weight; and a local blooming control module for: calculating an average luminance value of luminance levels of a plurality of pixels neighboring a pixel of the attenuated signal; operating a function on the average luminance value to generate a smoothly transitioning digital gain; conditioning the smoothly transitioning digital gain using said weight to generate a customizable digital gain; and applying the customizable digital gain to the attenuated signal.

Optionally, said weight comprises a first weight and a second weight. Still optionally, the reduced digital gain meets a condition where a sum of the first weight and the second weight is in the range of 1.0 to 5.0. Still optionally, the first weight is a constant value while the second weight has a value depending on surrounding luminance.

Optionally, the average luminance value is calculated using Gaussian weights.

Optionally, the function is a sigmoid function. Still optionally, a center point of the sigmoid function approximates 240/(1+second weight), wherein said viewing element of the endoscope comprises a CCD sensor. Still optionally, a center point of the sigmoid function approximates 255/(1+second weight), wherein said viewing element of the endoscope comprises a CMOS sensor. Still optionally, a center point of the sigmoid function approximates 100/(1+second weight), wherein said viewing element of the endoscope comprises a CMOS sensor. Still optionally, a center point of the sigmoid function decreases as the second weight increases and said center point increases as the second weight decreases.

In some embodiments, the customizable digital gain may meet a plurality of conditions, wherein said plurality of conditions may include at least one of: a value of said digital gain approaches 1.0 as a brightness of a region of the image frame nears maximal value; said digital gain has an upper limit of 5.0 in a region of the image frame that, relative to all other regions in said image frame, is darkest; or said digital gain transitions from a region of a first brightness to a region of a second brightness, wherein the first brightness is greater than the second brightness, in a smooth manner.

In some embodiments, the present specification discloses a method of controlling blooming in a plurality of regions of an image frame of a video data signal generated by a viewing element of an endoscope, said method being implemented by the controller of the endoscope, the method comprising: attenuating a luminance (Y) component of the video data signal to generate an attenuated signal, wherein the attenuation factor meets a condition such that a summation of a first weight $K_1$ and a second weight $K_2$ approximates a value equal to or less than 5.0; applying a Gaussian function to luminance levels of a plurality of pixels neighboring a given pixel of the attenuated signal to generate an average luminance signal Gaussian(Y); applying a sigmoid function to the average luminance signal to generate a modified signal sigmoid(Gaussian(Y)); and applying a digital gain to the attenuated signal, wherein the digital gain is determined by applying weights to the modified signal sigmoid (Gaussian(Y)).

Optionally, the weights comprise a first weight $K_1$ and a second weight $K_2$, wherein $K_1$ is a constant value and $K_2$ has a value depending on surrounding luminance.

Optionally, a center point of the sigmoid function approximates $240/(1+K_2)$, wherein said viewing element of the endoscope comprises a CCD sensor.

Optionally, a center point of the sigmoid function approximates 255/(1+second weight), wherein said viewing element of the endoscope comprises a CMOS sensor.

Optionally, a center point of the sigmoid function approximates 100/(1+second weight), wherein said viewing element of the endoscope comprises a CMOS sensor.

Optionally, a center point of the sigmoid function decreases as the second weight $K_2$ increases and said center point increases as the second weight $K_2$ decreases.

Optionally, the value of said digital gain approaches 1.0 as brightness of a region of the image frame nears maximum value.

Optionally, the value of said digital gain has an upper limit of 5.0 in a region of the image frame that, relative to all other regions in an image frame, is the darkest.

Optionally, said digital gain transitions from a region of a first brightness to a region of a second brightness, wherein the first brightness is greater than the second brightness, in a smooth manner.

In some embodiments, the present specification is directed toward an endoscope video processing system for controlling blooming in an image frame of a video data signal generated by a viewing element of an endoscope, to facilitate an increased luminance digital gain in regions of a first brightness within the image frame while maintaining a decreased luminance digital gain in regions of a second brightness, wherein the first brightness is lower than the second brightness, said video processing system comprising a processor and memory for executing the steps of: applying a reduced digital gain to a luminance (Y) component of the video data signal to generate an attenuated signal, wherein the reduced digital gain is defined by a weight; calculating an average luminance value of luminance levels of a plurality of pixels neighboring a pixel of the attenuated signal; operating a function on the average luminance value to generate a smoothly transitioning digital gain; conditioning the smoothly transitioning digital gain using said weight to generate a customizable digital gain; and applying the customizable digital gain to the attenuated signal.

The aforementioned and other embodiments of the present invention shall be described in greater depth in the drawings and detailed description provided below.

BRIEF DESCRIPTION OF THE DRAWINGS

These and other features and advantages of the present invention will be appreciated, as they become better understood by reference to the following detailed description when considered in connection with the accompanying drawings, wherein.

DETAILED DESCRIPTION

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

It is noted that the term "endoscope" as mentioned to herein may refer particularly to a colonoscope and a gastroscope, according to some embodiments, but is not limited only to colonoscopies and/or gastroscopies. The term "endoscope" may refer to any instrument used to examine the interior of a hollow organ or cavity of the body.

Figure 1:
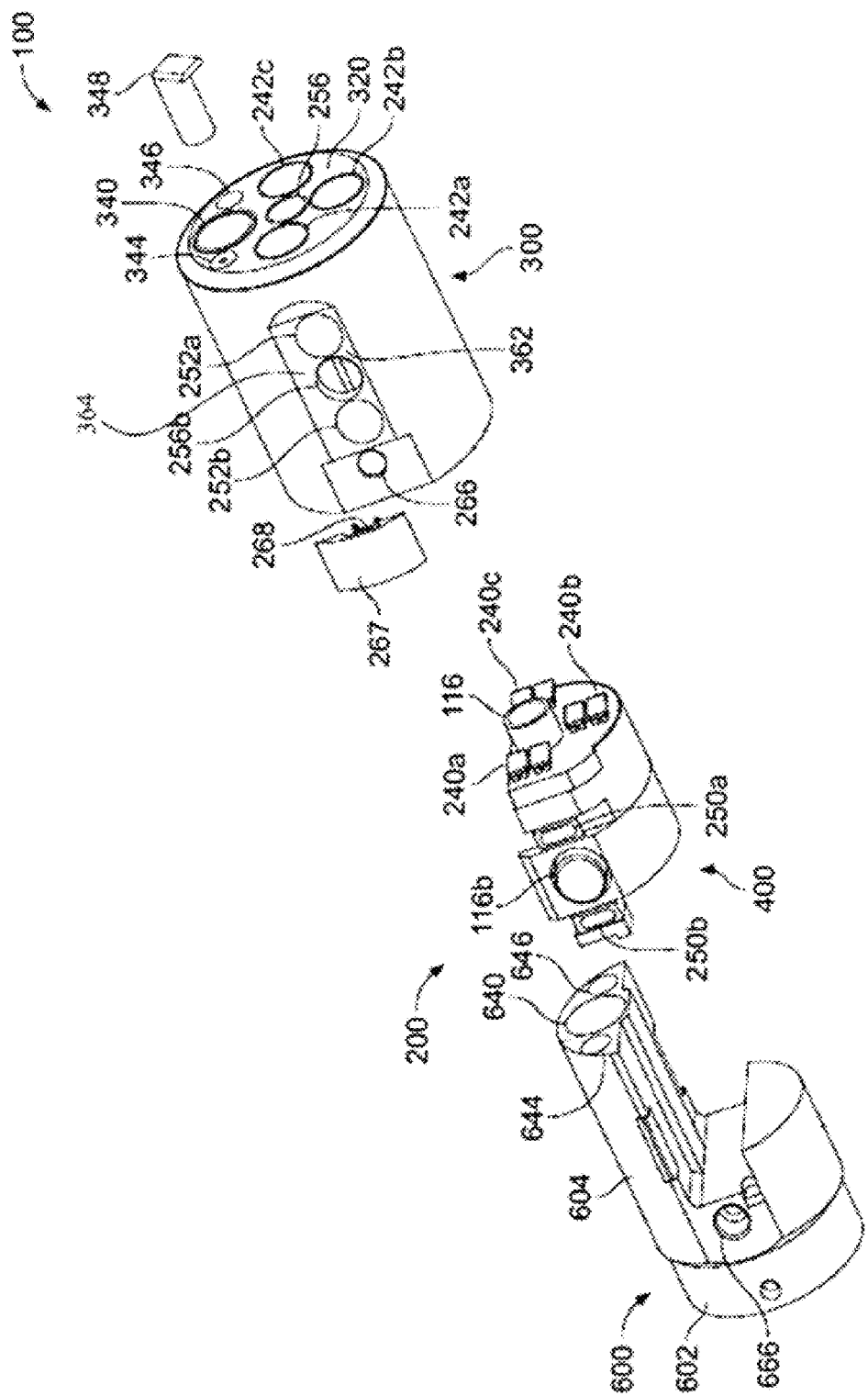
FIG. 1 shows an exploded view of a tip of a multiple viewing elements endoscope according to some embodiments.

FIG. 1 shows an exploded view of a tip section 200 of a multi-viewing element endoscope assembly 100 comprising a front working/service channel, according to various embodiments. An aspect of some embodiments also relates to endoscope assembly 100 having the tip section 200 that may be equipped with one or more side working/service channels. Accordingly, in an embodiment, tip section 200 of the endoscope 100 may include a tip cover 300, an electronic circuit board assembly 400 and a fluid channeling component 600.

Figure 2A:
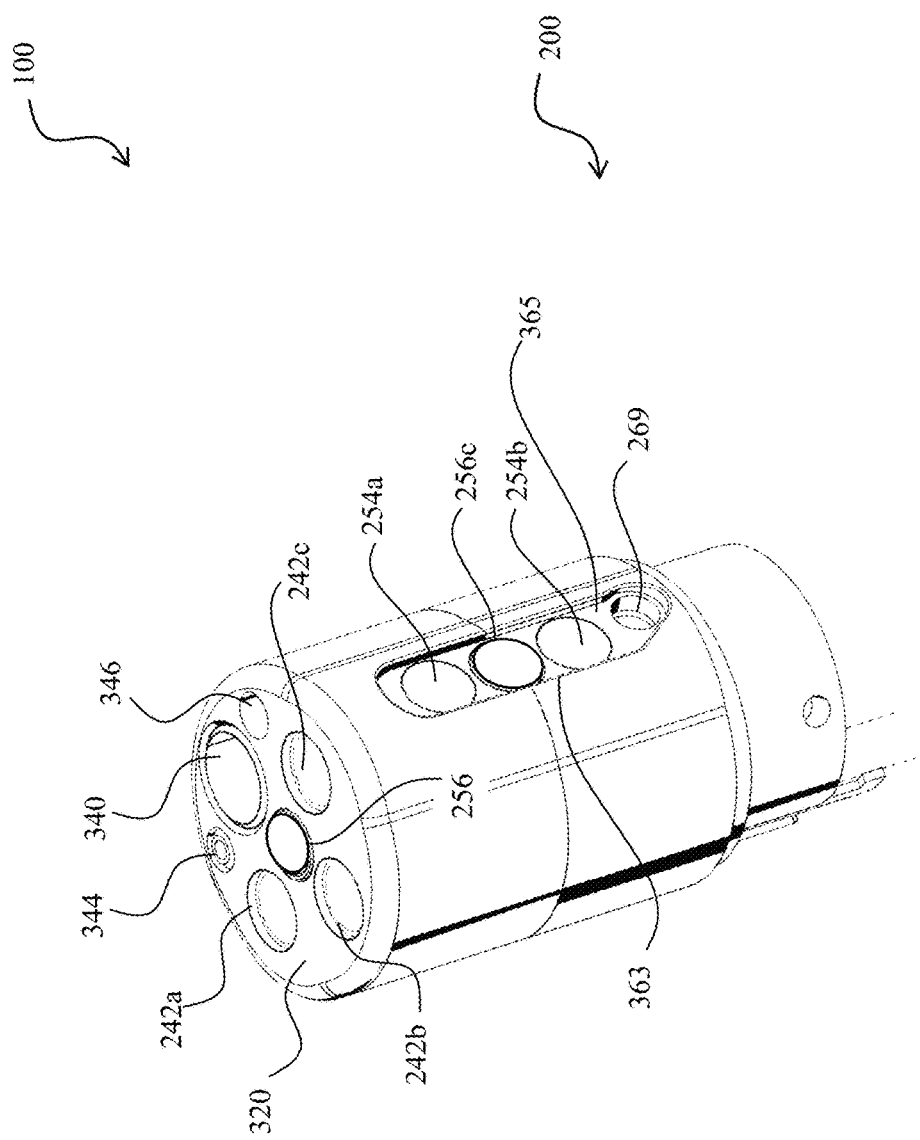
FIG. 2A shows a perspective view of the tip of the multiple viewing elements endoscope, of FIG. 1, according to some embodiments.
Figure 2B:
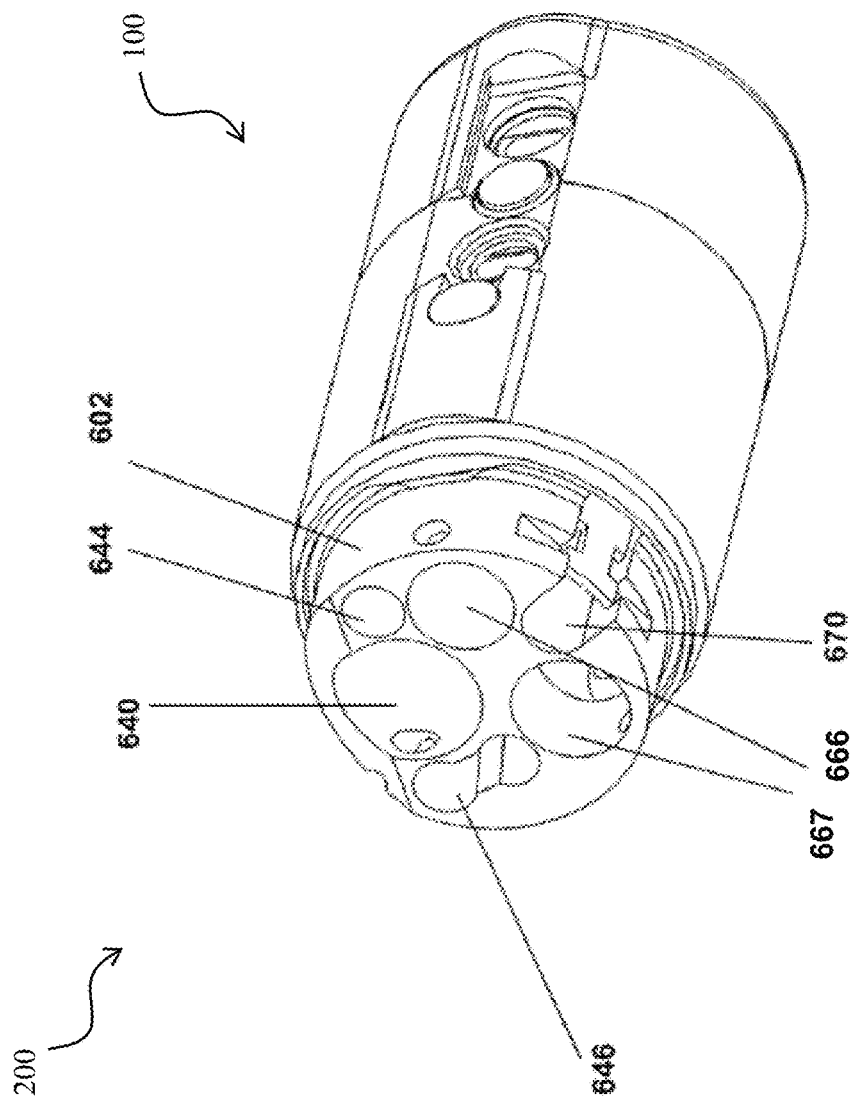
FIG. 2B shows another perspective view of the tip of the multiple viewing elements endoscope, of FIG. 1, according to some embodiments.

FIGS. 2A and 2B show perspective views of the tip section 200 according to an embodiment. Referring to FIGS. 1, 2A and 2B simultaneously, according to some embodiments, the tip section 200 includes a front panel 320 which comprises four quadrants defined by a vertical axis passing through a center of the front panel 320 and a horizontal axis passing through the center, wherein the four quadrants include a top left quadrant, a top right quadrant, a bottom left quadrant and a bottom right quadrant. In various embodiments, a transparent surface, window, or opening to front optical lens assembly 256 (of front looking camera or viewing element 116) is positioned on the front panel 320. In various embodiments, a first front optical window 242b, for a first front illuminator 240b, is positioned on the front panel 320, at least partially within the bottom right quadrant and at least partially within the bottom left quadrant. In various embodiments, a second front optical window 242a, for a second front illuminator 240a, is positioned on the front panel 320, at least partially within the bottom left quadrant. In various embodiments, a third front optical window 242c, for a third front illuminator 240c, is positioned on the front panel 320, at least partially within the bottom right quadrant.

In various embodiments, a front working channel opening 340, for working channel 640, is positioned on the front panel 320, along the vertical axis and at least partially within the top left quadrant and partially within the top right quadrant. In various embodiments, a fluid injector opening 346, for a fluid injector channel 646, is positioned on the front panel 320, at least partially within the top right quadrant. In various embodiments, a jet channel opening 344, for a jet channel 644, is positioned on the front panel 320, at least partially within the top left quadrant.

According to some embodiments, fluid channeling component 600 may include a proximal fluid channeling section 602 (or base) which may have an essentially cylindrical shape and a unitary distal channeling section 604 (or elongated housing). Distal fluid channeling section 604 may partially continue the cylindrical shape of proximal fluid channeling section 602 and may have a shape of a partial cylinder (optionally elongated partial cylinder). Distal fluid channeling section 604 may have only a fraction of the cylinder (along the height or length axis of the cylinder), wherein another fraction of the cylinder (along the height or length axis of the cylinder) is missing. In other words, in various embodiments, proximal fluid channeling section 602 has a greater width than distal fluid channeling section 604. Distal fluid channeling section 604 may be integrally formed as a unitary block with proximal fluid channeling section 602. The height or length of distal fluid channeling section 604 may by higher or longer than the height or length of proximal fluid channeling section 602. In the embodiment comprising distal fluid channeling section 604, the shape of the partial cylinder (for example, partial cylinder having only a fraction of a cylindrical shape along one side of the height axis) may provide a space to accommodate electronic circuit board assembly 400.

Distal fluid channeling section 604 includes working channel 640, which may be configured for insertion of a surgical tool, for example, to remove, treat and/or extract a sample of the object of interest found in the colon or its entirety for biopsy. Distal fluid channeling section 604 further includes the jet fluid channel 644 which may be configured for providing a high pressure jet of fluid, such as water or saline, for cleaning the walls of the body cavity (such as the colon) and optionally for suction. Distal fluid channeling section 604 further includes injector channel 646, which may be used for injecting fluid (liquid and/or gas) to wash contaminants such as blood, feces and other debris from a surface of front optical lens assembly 256 of forward-looking viewing element 116. Proximal fluid channeling section 602 of fluid channeling component 600 also includes side injector channel 666, which connects to side injector opening 266, and side injector channel 667 which connects to a similar side injector opening positioned on the opposite side of the tip section 200. The proximal fluid channeling section 602 also includes a groove 670 is adapted to guide (and optionally hold in place) an electric cable(s) which may be connected at its distal end to the electronic components such as viewing elements (for example, cameras) and/or light sources in the endoscope's tip section and deliver electrical power and/or command signals to the tip section and/or transmit video signal from the cameras to be displayed to the user.

Electronic circuit board assembly 400 may be configured to carry a front looking viewing element 116, a first side looking viewing element and a second side viewing element 116b which may be similar to front looking viewing element 116 and may include a Charge Coupled Device (CCD) or a Complementary Metal Oxide Semiconductor (CMOS) image sensor. The electronic circuit board assembly 400 may be configured to carry front illuminators 240a, 240b, 240c, which may be associated with front looking viewing element 116 and may be positioned to essentially illuminate the field of view of front looking viewing element 116.

In addition, electronic circuit board assembly 400 may be configured to carry side illuminators 250a and 250b, which may be associated with side looking viewing element 116b and may be positioned to essentially illuminate side looking viewing element's 116b field of view. Electronic circuit board assembly 400 may also be configured to carry side illuminators, which may be associated with the opposite side looking viewing element, which may be similar to side illuminators 250a and 250b.

Front illuminators 240a, 240b, 240c and side illuminators 250a and 250b may optionally be discrete illuminators and may include a light-emitting diode (LED), which may be a white light LED, an infrared light LED, a near infrared light LED, an ultraviolet light LED or any other LED.

The term "discrete", concerning discrete illuminator, may refer to an illumination source, which generates light internally, in contrast to a non-discrete illuminator, which may be, for example, a fiber optic merely transmitting light generated remotely.

Tip cover 300 may be configured to fit over the inner parts of the tip section 200 including electronic circuit board assembly 400 and fluid channeling component 600 and to provide protection to the internal components in the inner parts. Front optical lens assembly 256 may include a plurality of lenses, static or movable, which may provide a field of view of 90 degrees or more, 120 degrees or more or up to essentially 180 degrees. Front optical lens assembly 256 may provide a focal length in the range of about 3 to 100 millimeters. An optical axis of front looking camera or viewing element 116 may be essentially directed along the long dimension of the endoscope. However, since front looking camera or viewing element 116 is typically a wide angle camera, its field of view may include viewing directions at large angles to its optical axis.

Visible on the sidewall 362 of tip cover 300 is depression 364 wherein placed within depression 364 is side optical lens assembly 256b for side looking camera or viewing element 116b, which may be similar to front optical lens assembly 256, and optical windows 252a and 252b of illuminators 250a and 250b for side looking camera or viewing element 116b. On sidewall 363 of tip cover 300, on the opposing side to side optical lens assembly 256b, is a depression 365 and an optical lens assembly 256c for another side looking camera, which may be similar to side optical lens assembly 256b, and optical windows 254a and 254b for another set of illuminators similar to illuminators 250a and 250b. The side optical lens assemblies 256b, 256c may provide a focal length in the range of about 3 to 100 millimeters. In another embodiment, tip section 200 may include only one side viewing element.

An optical axis of the first side viewing element 116b may be essentially directed perpendicular to the long dimension of the endoscope. An optical axis of the second side viewing element may be essentially directed perpendicular to the long dimension of the endoscope. However, since each side viewing element typically comprises a wide angle camera, its field of view may include viewing directions at large angles to its optical axis. In accordance with some embodiments, each side viewing element has a field of view of 90 degrees or more, 120 degrees or more or up to essentially 180 degrees.

In addition, side injector opening 266 of side injector channel 666 may be located at a proximal end of sidewall 362 and side injector opening 269 of side injector 667 may be located at a proximal end of sidewall 363. A nozzle cover 267 may be configured to fit side injector opening 266 and a similar nozzle cover (not shown) may be configured to fit side injector opening 269.

Additionally, nozzle cover 267 may include a nozzle 268 which may be aimed at side optical lens assembly 256b and configured for injecting fluid to wash contaminants such as blood, feces and other debris from a surface of side optical lens assembly 256b of side looking camera or viewing element 116b. The fluid may include gas which may be used for inflating a body cavity. Optionally, nozzle 268 may be configured for cleaning both side optical lens assembly 256b and optical windows 252a and/or 252b.

It is noted that according to some embodiments, although tip section 200 is presented herein showing one side thereof, the opposing side may include elements similar to the side elements described herein (for example, side looking camera, side optical lens assembly, injector(s), nozzle(s), illuminator(s), window(s), opening(s) and other elements).

Figure 3:
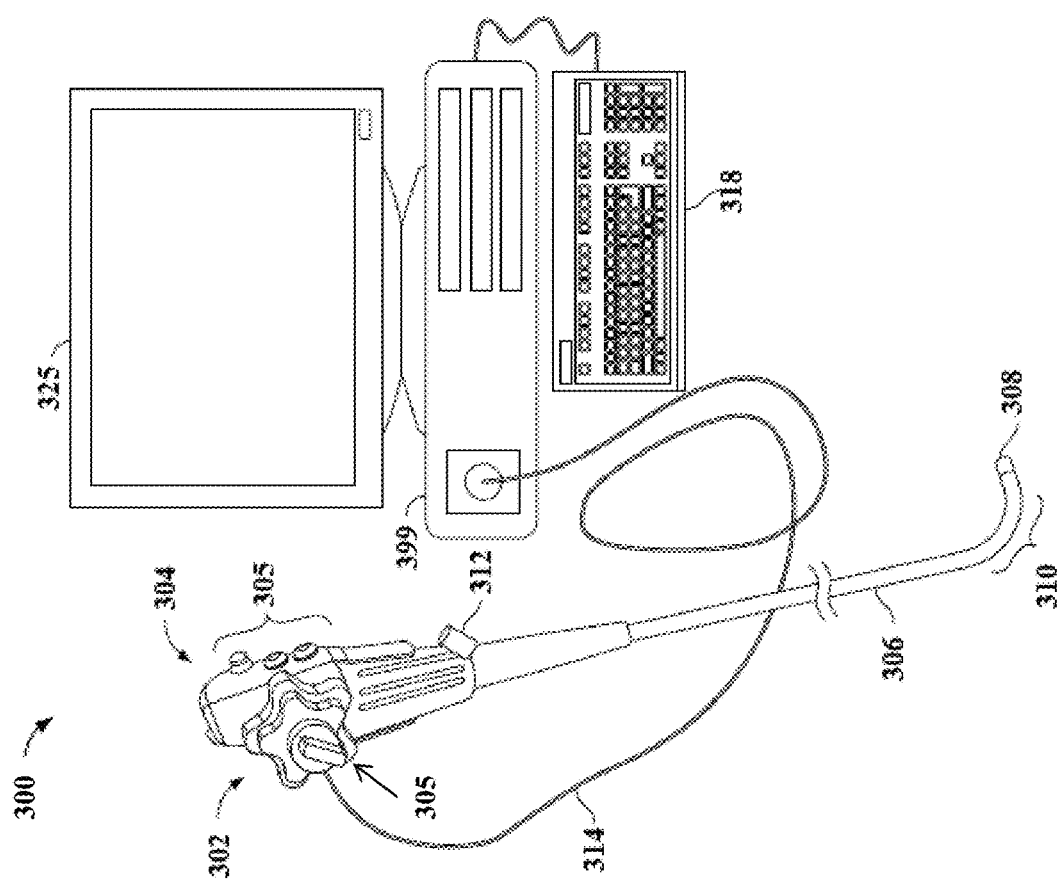
FIG. 3 shows a multiple viewing elements endoscopy system, according to some embodiments.

Reference is now made to FIG. 3, which shows an exemplary multi-viewing elements endoscopy system 300. System 300 may include a multi-viewing elements endoscope 302. Multi-viewing elements endoscope 302 may include a handle 304, from which an elongated shaft 306 emerges. Elongated shaft 306 terminates with a tip section 308 which is turnable by way of a bending section 310. Handle 304 may be used for maneuvering elongated shaft 306 within a body cavity. The handle may include one or more buttons and/or knobs and/or switches 305 which control bending section 310 as well as functions such as fluid injection and suction. Handle 304 may further include at least one, and in some embodiments, one or more working channel openings 312 through which surgical tools may be inserted as well as one and more side service channel openings.

A utility cable 314, also referred to as an umbilical tube, may connect between handle 304 and a Main Control Unit 399. Utility cable 314 may include therein one or more fluid channels and one or more electrical channels. The electrical channel(s) may include at least one data cable for receiving video signals from the front and side-pointing viewing elements, as well as at least one power cable for providing electrical power to the viewing elements and to the discrete illuminators.

The main control unit 399 contains the controls required for displaying the images of internal organs captured by the endoscope 302. The main control unit 399 may govern power transmission to the endoscope's 302 tip section 308, such as for the tip section's viewing elements and illuminators. The main control unit 399 may further control one or more fluid, liquid and/or suction pump(s) which supply corresponding functionalities to the endoscope 302. One or more input devices 318, such as a keyboard, a touch screen and the like may be connected to the main control unit 399 for the purpose of human interaction with the main control unit 399. In the embodiment shown in FIG. 3, the main control unit 399 comprises a screen/display 325 for displaying operation information concerning an endoscopy procedure when the endoscope 302 is in use. The screen 325 may be configured to display images and/or video streams received from the viewing elements of the multi-viewing element endoscope 302. The screen 325 may further be operative to display a user interface for allowing a human operator to set various features of the endoscopy system.

Optionally, the video streams received from the different viewing elements of the multi-viewing element endoscope 302 may be displayed separately on at least one monitor (not seen) by uploading information from the main control unit 399, either side-by-side or interchangeably (namely, the operator may switch between views from the different viewing elements manually). Alternatively, these video streams may be processed by the main control unit 399 to combine them into a single, panoramic video frame, based on an overlap between fields of view of the viewing elements. In an embodiment, two or more displays may be connected to the main control unit 399, each for displaying a video stream from a different viewing element of the multi-viewing element endoscope 302. The main control unit 399 is described in U.S. patent application Ser. No. 14/263,896, which, for priority, relies on U.S. Provisional Patent Application No. 61/817,237, entitled "Method and System for Video Processing in a Multi-Viewing Element Endoscope" and filed on Apr. 29, 2013, which is herein incorporated by reference in its entirety.

Figure 4:
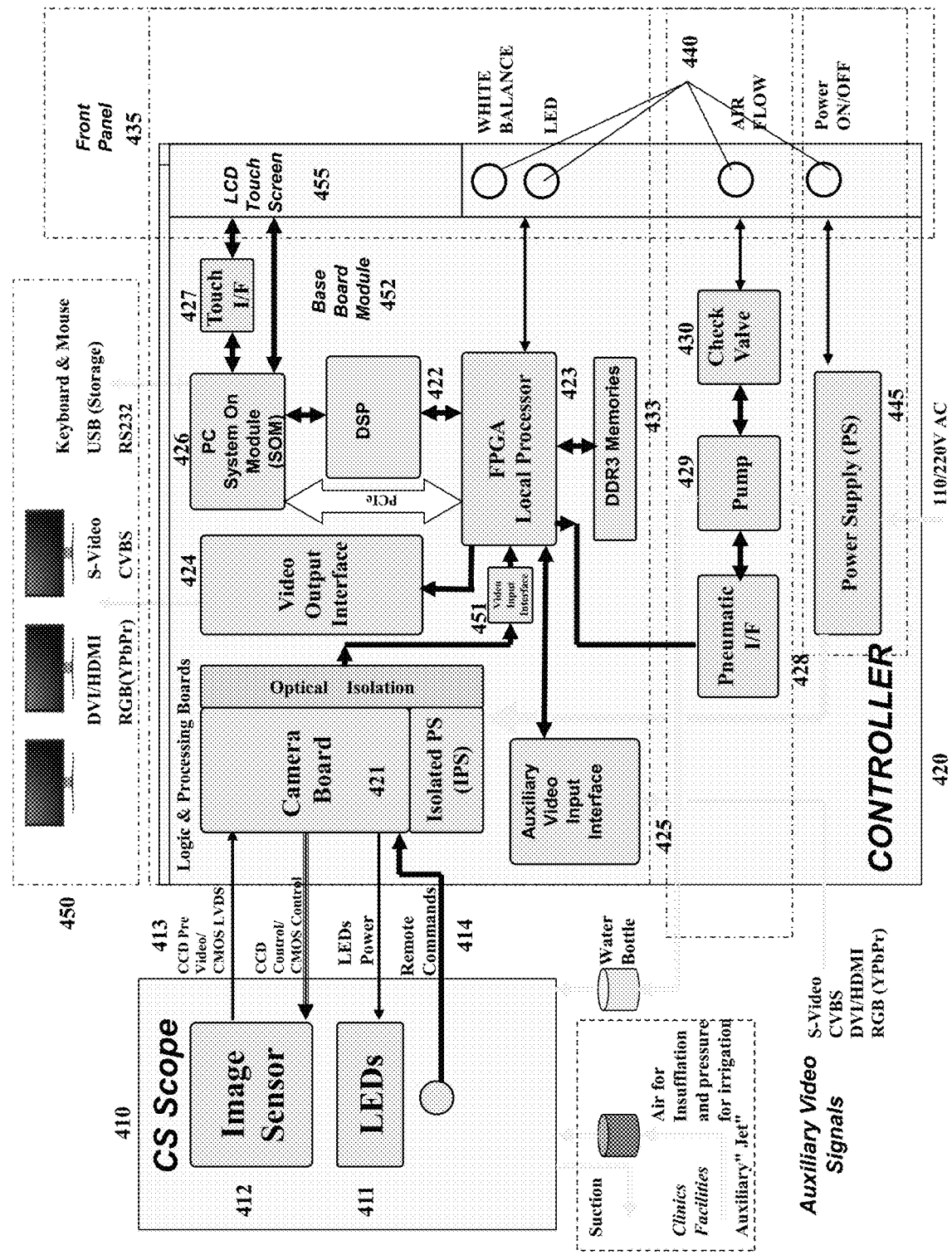
FIG. 4 is a block diagram illustrating overall video processing architecture within an endoscopy system.

FIG. 4 details how the video controller or the controller circuit board 420 of the main control unit 399 of FIG. 3 operatively connects with the endoscope 410 and the display units 450, according to one embodiment. Referring to FIG. 4, video controller/controller circuit board 420 comprises a camera board 421 that controls the power supplies to the LEDs 411, transmits controls for the operation of image sensor(s) 412 (comprising one or more cameras) in the endoscope, and converts pre-video signals from image sensors to standard video signals. The image sensor 412 may be a charge coupled device (CCD) or a complementary metal oxide semiconductor (CMOS) imager. The camera board 421 receives pre-video signal(s) 413 generated by the CCD imager and also other remote commands 414 from the endoscope 410.

Controller circuit board 420 further comprises elements for processing the video obtained from the image sensors 412 through the camera board 421, as well as other elements for system monitoring and control.

All these elements are connected with the Base Board Module 452, which is a PCB. In one embodiment, elements which are ICs (Integrated Circuits) are connected by soldering, element 426 (SOM or System on Module) is connected by mounting, while all other elements are connected by means of cables.

Various elements on the Base Board Module 452 are described as follows:
FPGA (Field Programmable Gate Array) 423:

FPGA 423 is a logic device programmed specifically for the system requirements and performs tasks that may be categorized by two types: logic tasks which must be implemented by hardware (as opposed to software), and logic tasks related to video image processing. In one embodiment, the Base Board Module 452 includes one or more double data rate type three synchronous dynamic random access memory modules (DDR3) 433 in communication with the FPGA 423.

Logic tasks which are preferably implemented by hardware include, but are not limited to:
1. Initializing some Base Board Module's 452 ICs upon system power-up;

2. Monitoring the buttons 440 for white balance, the on/off state of the LEDs, air flow, and power on/off on the front-panel 435;
3. Monitoring SOM's 426 proper operation using a watch-dog mechanism;
4. Backing-up some of the system's parameters (example: airflow level), even while the system is switched off; and
5. Communicating with the camera board 421.

Logic tasks related to video image processing include, but are not limited to:
1. Multiplexing video inputs—Each of the multiple imaging elements has several video interfaces which are multiplexed via a video input interface 451. Further, several auxiliaries are multiplexed via auxiliary video input interface 425. For example, a physician's laptop may be connected as an auxiliary video source to the endoscope system, and a recorded procedure may be played on the system screen. As another example, video output of an X-Ray imaging system may be connected via the auxiliary video input interface 425, so that the physician is able to see the image generated by the endoscope's viewing elements as well as the related X-Ray image side by side or in PIP (Picture-in-Picture) on the same screen. Accordingly, an auxiliary video source, such as an external laptop playing a recorded procedure or a video output of an X-ray system, may be multiplexed with video outputs of each of the multiple imaging elements.
2. Optional digital signal processor (DSP) 422 playback output and DSP record input.
3. Internal test patterns to video outputs via Video Output Interface 424 to multiple displays. In one embodiment an internal test pattern comprises an artificial image composed of lines, stationary boxes, moving boxes or other geometric patterns of different colors and sizes. Such a test pattern enables an engineer to test the system's output video performance without being dependent on the performance of the endoscope's viewing elements. In one embodiment, an internal test pattern is used to generate an image which is more challenging for the video processing system to process and display compared to the images generated by viewing elements. In some embodiments, an internal test pattern is displayed on the screen whenever an endoscope is not connected to the main control unit.
4. Conversion between cameras' video standard to display according to one video standard.
5. OSD (On Screen Display) insertion, also known as graphic overlay.
6. Generating PIP (Picture-in-Picture).
7. Stitching images from several cameras into one image displayed on a single screen.
8. Image adjustments, such as brightness, sharpness, color saturation and contrast.

DSP (Digital Signal Processor) 422:

DSP 422 is used for recording compressed (coded) video and playing back decompressed (decoded) video. In one embodiment, the standard of compressed video is H264 or equivalent (such as MPEG).

Operationally, FPGA 423 selects for the DSP 422 the desired video to be recorded, i.e. any of the inputs, or, more likely, a copy of one or more of the screens. In the latter case, this includes the OSD and format conversion. In the likely case of the screen's format differing from that of DSP's 422 required video input format, the FPGA 423 also converts the screen's format to the desired DSP 422 format while transmitting video to the DSP 422.

Auxiliary Video Input Interface 425:

In one embodiment, the video input to the Auxiliary Video Input Interface 425 may comprise analog video, such as in CVBS (color, video, blanking, sync), S-Video or YPbPr format or digital video (DVI), and may be displayed as such.

SOM (System on Module) 426:

The SOM 426 provides an interface to input devices such as keyboard, mouse, and touchscreen via Touch I/F 427. Through these input devices, together with the buttons 440 in the Front Panel 435, the user controls the system's functionality and operational parameters. In one embodiment, a peripheral component interconnect express (PCIe) bus connects the SOM 426 with the FPGA 423. Most common types of data traffic over the PCIe are:
1. SOM 426 to FPGA 423: Commands (for example, when the user changes operational parameters); and
2. FPGA 423 to SOM 426: Registers values, which provide an indication of the internal status, and captured images.

Video Processing

The controller circuit board 420 may further control one or more fluid, liquid and/or suction pump(s) which supply corresponding functionalities to the endoscope through pneumatic I/F 428, pump 429 and check valve 430. The controller circuit board 420 further comprises an on-board power supply 445 and a front panel 435 which provides operational buttons 440 for the user.

Figure 5A:
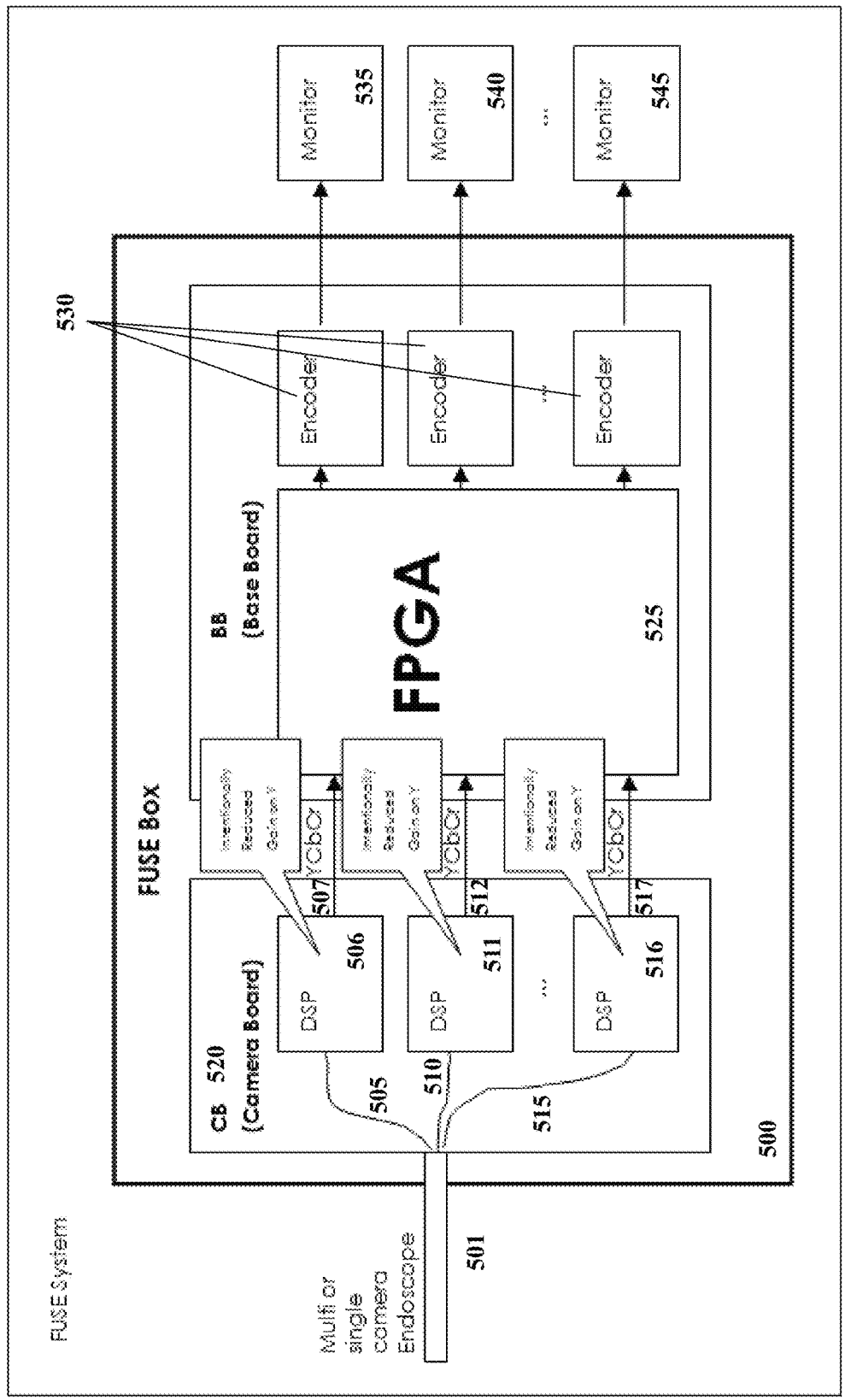
FIG. 5A is a simplified view of the video processing block diagram shown in FIG. 4.

FIG. 5A is another illustration of the video controller or the controller circuit board 500 of the main control unit 399 of FIG. 3. Referring now to FIG. 5A, the camera board 520 receives video signals which, in one embodiment, comprises three video feeds, corresponding to video feed pickups by three endoscopic tip viewing elements (one front and two side-looking viewing elements), as generated by the image sensor 412 (FIG. 4). In one embodiment, the video feed pickups are separated into three different video feeds/data streams 505, 510, and 515 for processing by respective Digital Signal Processors (DSPs) 506, 511 and 516. The video data streams 507, 512 and 517 (corresponding to the three viewing elements) output from the DSPs 506, 511, 516 respectively comprise a luminance component (Y), a blue-difference ($C_B$) chroma component, and a red-difference ($C_R$) chroma component. The Y, $C_B$, and $C_R$ components form input feeds to the FPGA 525. In one embodiment, the three video feed/data streams 507, 512 and 517, corresponding to the three viewing elements (the front-looking, left-side looking and right-side looking viewing elements) of an endoscopic tip 501 (such as the three viewing elements of the tip section 200 of FIG. 1), are processed by the FPGA 525, encoded (for example, serialization of video data into HDMI/DVI serial lines) using encoders 530 and thereafter displayed on three respective monitors 535, 540 and 545.

As discussed earlier (with reference to FIG. 4) the FPGA 525 performs a plurality of logic tasks related to video stream/image processing—one of which includes brightness and/or blooming control. To avoid blooming or saturation, the DSPs 506, 511, 516 apply a reduced gain on the luminance (Y) components of the video data streams 505, 510, 515 so that the corresponding output video data streams 507, 512, 517 meet an anti-blooming condition/constraint. In one embodiment, the anti-blooming condition, constraint, or restriction is that a respective Y component is not saturated even when the corresponding image is very bright. This ensures that even in the brightest parts of an image the Y component value remains lower than 255 (since, Y, $C_B$ and $C_R$ are each 8-bit) by a safe margin so that image details are perceivable to a viewer. In one embodiment, to meet or satisfy the anti-blooming condition/constraint the DSPs 506, 511, 516 the Y (luminance) components of the three video data streams 505, 510, 515 are attenuated by a factor of:

$$K_1 + K_2 \sim 1.5,$$

where $K_1$ represents an element of the gain which is constant, not depending on surrounding luminance, and $K_2$ represents a weight attributed to the surrounding luminance. In one embodiment, $K_1$ is 1.00 and $K_1 + K_2 \sim 1.5$. In one embodiment $K_1 + K_2$ equals a range of 1.0 to 5.0.

As a result of the application of the aforementioned anti-blooming condition, parts of the image whose brightness is normal or lower may appear to the viewer as dimmed, perhaps even with some loss of details in darker parts. A less preferred solution to this dimming effect can be to have the FPGA 525 add a digital gain to the Y component, wherein the gain may vary every image frame according to the total average brightness of that frame. However, this would still cause blooming in image frames where there are only small portions of very high luminance, thereby having very little effect on the average brightness. Conversely, in bright image frames with small dark portions, the dimming effect may still persist—with possible loss in image details.

In accordance with an aspect of the present specification, a local blooming control (LBC) module is implemented to facilitate a higher luminance digital gain in darker portions while maintaining a low or no luminance digital gain in brighter portions, within the same image frame. In one embodiment, the LBC module implements the following processing steps and conditions:

Around every luminance pixel sample, $Y_{CB}$, arriving from the camera board (CB) 520 a Gaussian function (averaging process using Gaussian weighing) of its neighborhood pixels is calculated. Hence, the output of the Gaussian function is the local brightness around $Y_{CB}$. In an embodiment, the Gaussian function is implemented as a 2D kernel which is symmetric and separable, with a size range of 9V×15 H. It may be noted that the size range depends on the resolution of the image sensor(s) or the viewing element(s) of the endoscope. As sensor's resolution increases, so does the 2D kernel. A larger kernel can be implemented by either increasing 2D matrix's size, or, by cascading two or more 9V×15 H kernels, to yield kernels having a size of 30V×30 H or more. It may further be noted that while the term Gaussian function is used, any function adapted to yield a curved distribution, or "normal distribution", of values may be used.

With the pixels of a frame mapped in terms of a Gaussian function, areas of higher Gaussian values are assigned lower/lesser digital gains than areas of lower Gaussians values. The digital gain complies with the following three conditions, in accordance with an embodiment:
1. Approaches 1.0, as brightness nears maximal value;
2. Upper-limited to 5.0, even in the darkest areas; and
3. Transitions from bright areas to dark areas in a smooth manner.

To meet the aforementioned three conditions, a sigmoid function operates on the outputs of the Gaussian function. While the present application discusses the invention in terms of applying a sigmoid function, it should be appreciated that other mathematical functions have an S shaped (or sigmoid curve) may be applied. Thus, in accordance with an embodiment, an overall output of the LBC module is defined as:

$$Y_{LBC} = 16 + (Y_{CB} - 16) \times (K_1 + K_2 \times \text{Sigmoid(Gaussian)})$$

where, $K_1 + K_2 \times$ Sigmoid (Gaussian) is the gain operating on the luminance component ($Y_{CB}$) of a given pixel. It should be appreciated that this gain is dynamic and depends on the overall average luminance level over the vicinity of the given pixel.

Figure 6:
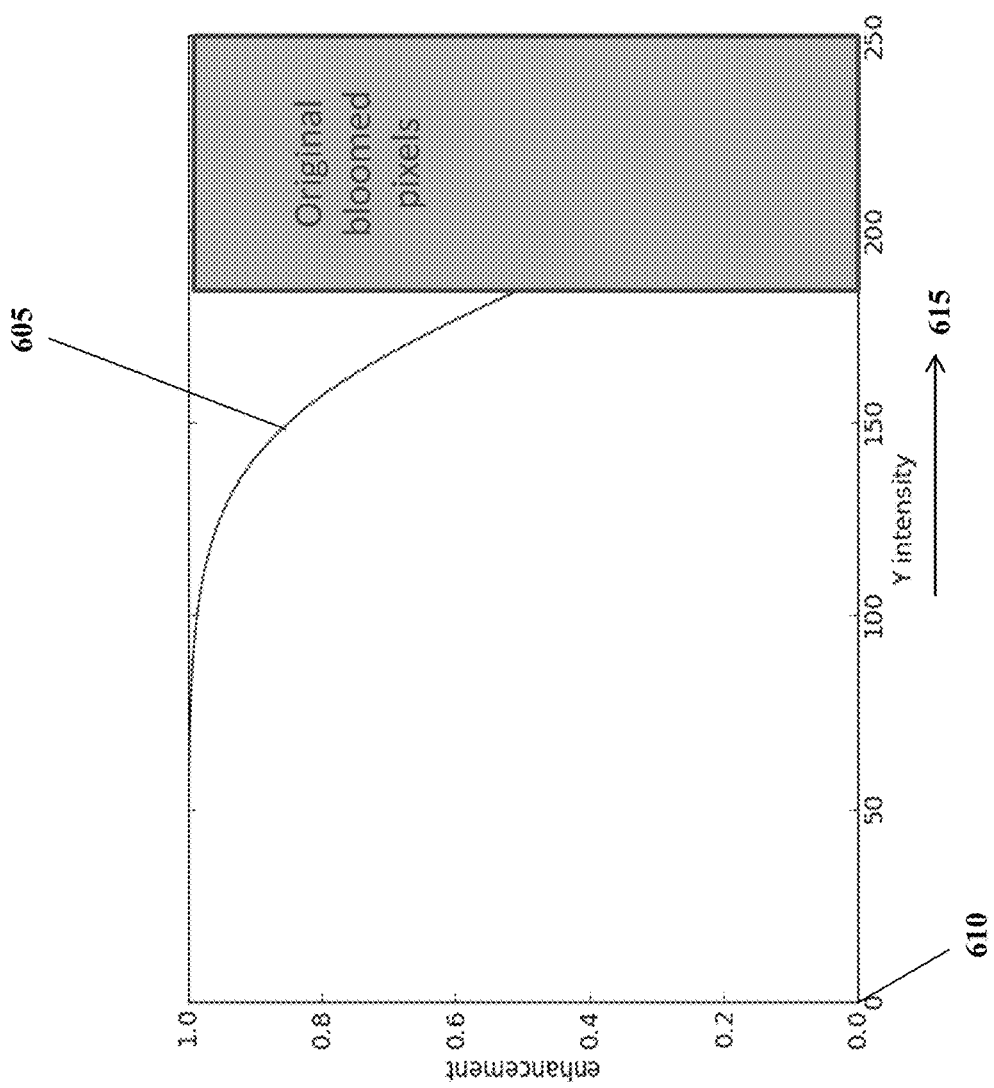
FIG. 6 is a graphical illustration of an exemplary sigmoid function.

As discussed earlier, averaging of luminance levels of neighboring pixels is done with Gaussian weighing. This average luminance level feeds a sigmoid function, an example of which is illustrated in FIG. 6. As shown in FIG. 6, the sigmoid 605 (operating on the Gaussian for $K_2$=0.30 as an example case) approaches 1 at minimal luminance levels 610, and gradually drops to 0 as luminance levels increase (as illustrated in the direction of the arrow 615 along the x-axis). Therefore, at high luminance levels, the gain approaches $K_1$ (sigmoid nears 0) whereas at low luminance levels, the gain approaches $K_1 + K_2$ (sigmoid nears 1). As defined above, $K_1$ represents an element of the gain which is constant, and independent of the surrounding luminance. In one embodiment, it is 1.00. $K_2$ represents a weight attributed to the surrounding luminance. In a preferred embodiment, $K_1$=1.00 and $K_2$=0.50 such that $K_1 + K_2 \sim 5.0$. Persons of ordinary skill in the art appreciate that these preferred values of $K_1$=1.00 and $K_2$=0.50 represent one out of a plurality of values leading to various alternate embodiments that provide good visual results in terms of blooming control.

Figure 5B:
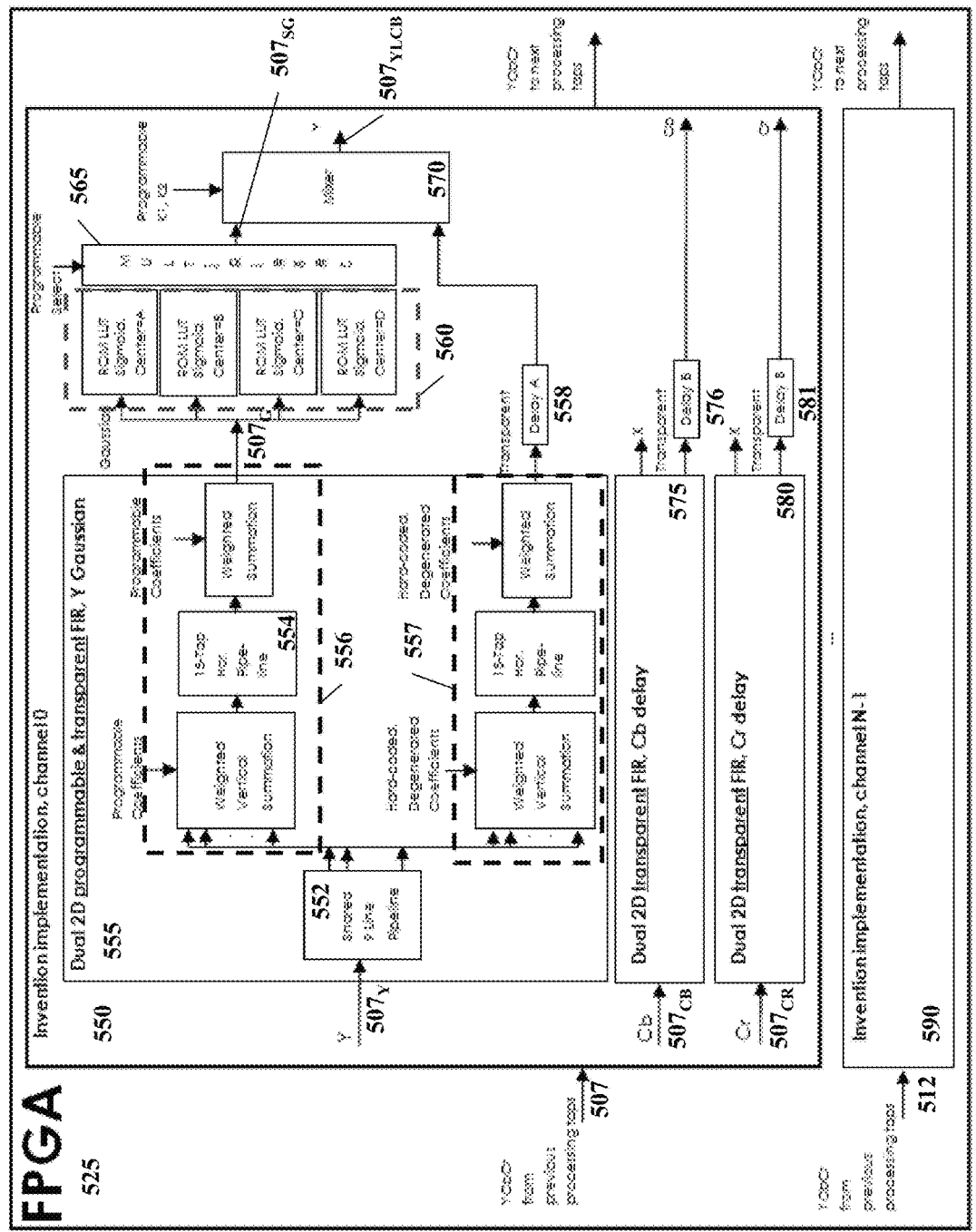
FIG. 5B is a block diagram illustrating implementation of a local blooming control (LBC) module.

FIG. 5B is a block diagram illustrating implementation of a local blooming control (LBC) module 550 within the FPGA 525, in accordance with various embodiments of the present specification. Persons of ordinary skill in the art should appreciate that the LBC module 550 can be implemented either as firmware (FPGA) or software executing in a general processor. In the former case, the parameters affecting the LBC operation may be either hard-coded to spare firmware resources or programmable to enable flexibility. Referring now to FIGS. 5A and 5B simultaneously, a video feed/data stream, such as stream 507 output from the camera board 520, arrives as input stream to the FPGA 525. The Y (luminance) component 507$_Y$ of the input data stream 507 is fed into a dual 2D (two dimensional) programmable and transparent FIR (Finite Impulse Response) filter 555 to apply a Gaussian function around the Y component 507$_Y$, as described above, resulting in an output Gaussian (Y) signal 507$_G$.

In accordance with an embodiment, the 2D FIR filter 555 comprises a pipeline of programmable (or hard-coded) coefficients 556 for Gaussian calculation. Persons of ordinary skill in the art should appreciate that the size of the 2D FIR filter 555 chosen depends at least on a combination of and optimization between: a) available FPGA resources such as memory cells and arithmetic modules and b) the required size of the image frame region over which luminance average is calculated. In a preferred embodiment, the 2D FIR filter 555 size comprises 9V×15 H (9 lines by 15 pixels) which is the reason why FIG. 5B illustrates the Y component 507$_Y$ being fed through a shared 9 tap vertical pipeline 552 while the programmable coefficients 556 include weighted vertical summation for a 15 tap horizontal pipeline 554. However, alternate embodiments may have different sizes for the 2D FIR filter 555 as would be advantageously evident to persons of ordinary skill in the art. In one embodiment, the maximum size of the 2D FIR filter is in the range of 30V×30 H.

In one embodiment, the 2D FIR filter 555 is of the type which is both separable and symmetric. A separable 2D-FIR filter is implementable as two separate 1D-FIR filters, one for the vertical axis and the other for the horizontal axis. This architecture for the 2D-FIR filter is preferred since the intended weighting is Gaussian, which is 2D-separable (Gaussian($\sqrt{(X^2+Y^2)}$)=Gaussian1(X)×Gaussian2(Y)). However, alternate embodiments may utilize other types of 2D-FIR filters such as, for example, a non-separable filter. Also, the use of Dual 2D-FIR filter provides for a future use of the secondary 2D-FIR such as, for example, for implementing an image sharpening function. However, in alternate embodiments, the Dual 2D-FIR filter is replaced with a single modified 2D-FIR filter that outputs the central pixel of its matrix as-is, in addition to the Gaussian.

The output Gaussian(Y) signal $507_G$ forms an input to a plurality of ROM-based LUTs (Look-Up Tables) 560 (to implement a sigmoid function on signal $507_G$) driving a programmable multiplexer 565. In one embodiment, as shown in FIG. 5B, a four ROM-based LUT system 560 is used for implementing the sigmoid function. However, alternate embodiments have ROMs more or less than four. In an alternate embodiment, instead of multiple ROMs, a single programmable RAM-based LUT (Look-Up Table) is implemented that is programmable (by software/firmware) in real-time for any sigmoid type. The multiplexer 565 outputs a sigmoid (Gaussian(Y)) signal $507_{SG}$. In a preferred embodiment, the sigmoid function is so selected such that its center point approximates $240/(1+K_2)$, that is—the center point moves towards the left (decreases) as $K_2$ increases, and vice versa. It may be noted that the value "240" depends on the type of image sensor being used. For example, in case of CCD sensors, 240 represents the upper limit for Y (luminance) component of the YCbCr color space. For CMOS sensors, other color spaces, such as LAB may be used, which require a different value as the maximum limit of the luminance component. In one embodiment, the value chosen as maximum limit of luminance component in case of CMOS sensors is either 100 or 255. In one embodiment, the chosen value of maximum limit is hardwired to a register. In another embodiment, the value of maximum limit is added to the FPGA logic and the system software, such that it can be altered depending upon the type of image sensor used. In another embodiment, the sigmoid function is selected such that its center point approximates $X/(1+K_2)$ where X is indicative of a Y component of a color space specific to a type of image sensor being used.

In accordance with an embodiment, a pipeline 557 of coefficients and delay component 558 participates in delaying the original Y component $507_Y$ so that when it reaches the mixer 570, it is aligned with the sigmoid (Gaussian(Y)) signal $507_{SG}$. Thus, the original Y component $507_Y$ and the sigmoid (Gaussian(Y)) signal $507_{SG}$ are aligned when they reach the mixer 570. The mixer 570 is programmable, in accordance with an embodiment, with weights $K_1$ and $K_2$ so as to apply a gain $K_1+K_2\times$sigmoid (Gaussian) on the Y component $507_Y$ and output a blooming controlled Y component $507_{YLCB}$.

The $C_B$ and $C_R$ Chroma components $507_{CB}$, $507_{CR}$ of the input data stream 507 are respectively fed into a first and a second dual 2D (two dimensional) transparent FIR (Finite Impulse Response) filter 575, 580. Persons of ordinary skill in the art would note that in transparent FIR filters (such as FIR filters 575, 580) coefficients are degenerated, that is all coefficients are null, except for the central one which is unity. Thus, FIR output is identical to its input, but with the addition of a delay. Accordingly, the filters 575, 580 and the respective delay components 576, 581 apply latency to the $C_B$ and $C_R$ components $507_{CB}$ and $507_{CR}$, to align them with the signal $507_{SG}$. It should be appreciated, however, that delaying of the $C_B$ and $C_R$ components $507_{CB}$ and $507_{CR}$ is required only if they share the same synchronization signals with the Y component $507_Y$.

In one embodiment, a first LBC module 550 applies a managed luminance gain to the video feed/data stream 507, as described above. Similarly, additional LBC modules (such as for example module 590), are implemented to manage application of luminance gain to the corresponding additional video feed/data streams 512, 517 (FIG. 5A). In other words, the number of LBC modules depends upon the number of video feeds/data streams and therefore the number of viewing elements of the endoscopic tip.

Figure 7:
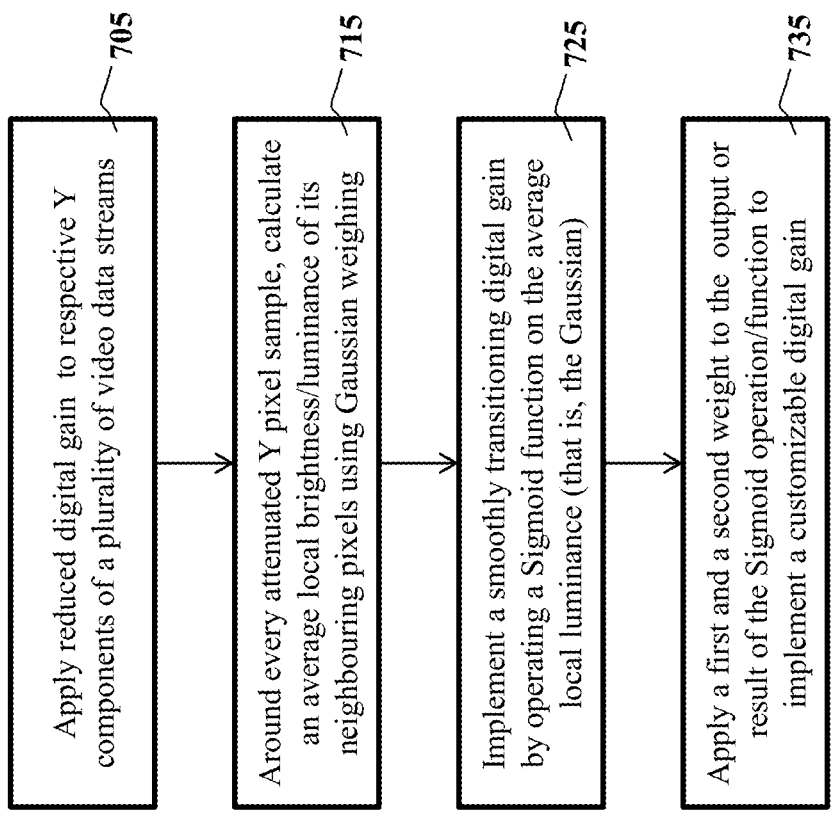
FIG. 7 is a flow chart illustrating a plurality of exemplary steps of a brightness, luminance or blooming control method in accordance with an embodiment of the present specification.

FIG. 7 is a flow chart illustrating a plurality of exemplary steps of a brightness, luminance or blooming control method in accordance with an embodiment of the present specification. At step 705, a reduced digital gain or attenuation is applied to respective Y (luminance) components of a plurality of video data streams (such as for example three video data streams generated by a multi-viewing elements endoscope) to output respective Y-attenuated output video streams. In one embodiment, the Y components are attenuated by a factor of $K_1+K_2\sim1.5$ so that the Y components are not saturated even when the corresponding images are very bright. The attenuated video data streams, output as a result of step 705, are respectively processed to facilitate a higher luminance digital gain in darker portions while maintaining a low or no luminance digital gain in brighter portions, within the same image frame.

Thus, at step 715, around every Y (luminance) pixel sample of the Y-attenuated output video streams, an average local brightness/luminance of its neighboring pixels is calculated. In one embodiment, the averaging is done using Gaussian weights. The output Gaussian of the neighboring pixels is utilized to develop/implement a smoothly transitioning digital gain at step 725, such that areas of higher Gaussians are assigned higher digital gains than areas of lower Gaussians. It may be noted that a transition is smooth if it has continuous derivatives up to some order over the domain of values. The number of continuous derivatives necessary for a function to be considered smooth is two or greater. Thus, a smoothly transitioning gain is defined as a gain that transitions from bright areas to dark areas in a smooth manner. In one embodiment, the smoothly transitioning digital gain is implemented by operating a sigmoid function on the output Gaussian of step 715. At step, 735, the sigmoid function is further weighed or conditioned to apply a customizable digital gain. In one embodiment, the customizable digital gain applied meets the following conditions:

Approaches 1.0, as brightness nears maximal value;
Upper-limited to 1.5, even in the darkest areas; and
Transitions from bright areas to dark areas, in a smooth manner.

Accordingly, in accordance with an embodiment, the customizable digital gain is calculated as $K_1+K_2\times$sigmoid (Gaussian(Y)), where $K_1$ and $K_2$ are a first and a second weights operating on an output/result of the sigmoid function/operation. $K_1$ represents an element of the gain which is constant and independent of the surrounding luminance. $K_1$ is 1.00 in one embodiment. $K_2$ represents a weight attributed to the surrounding luminance. In a preferred embodiment, $K_1=1.00$ and $K_2=0.50$ such that $K_1+K_2\sim1.5$. Persons of ordinary skill in the art should appreciate that these preferred values of $K_1=1.00$ and $K_2=0.50$ represent one out of a plurality of values leading to various alternate embodiments that provide good visual results in terms of blooming control.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

In the description and claims of the application, each of the words "comprise" "include" and "have", and forms thereof, are not necessarily limited to members in a list with which the words may be associated.

We claim:

1. An endoscope video processing system, comprising:
   a viewing element of an endoscope for generating a video data signal having an image frame, wherein the viewing element includes an image sensor;
   a processor in communication with the viewing element;
   a memory in communication with at least one of the viewing element and the processor;
   a digital signal processor in communication with at least one of the viewing element, the processor, and the memory, for applying a reduced digital gain to a luminance (Y) component of the video data signal generated by the viewing element of the endoscope to generate an attenuated signal, wherein the reduced digital gain is defined by a weight; and
   a local blooming control module for:
      calculating an average luminance value of luminance levels of a plurality of pixels neighboring a pixel of the attenuated signal;
      operating a function on the average luminance value to generate a smoothly transitioning digital gain, wherein the function is a sigmoid function;
      conditioning the smoothly transitioning digital gain using said weight to generate a customizable digital gain; and
      applying the customizable digital gain to the attenuated signal, for controlling blooming in the image frame of the video data signal generated by the viewing element of the endoscope, to facilitate an increased luminance digital gain in regions of a first brightness within the image frame while maintaining a decreased luminance digital gain in regions of a second brightness, wherein the first brightness is lower than the second brightness.

2. The endoscope video processing system of claim 1, wherein said weight comprises a first weight and a second weight.

3. The endoscope video processing system of claim 2, wherein the reduced digital gain meets a condition where a sum of the first weight and the second weight is in the range of 1.0 to 5.0.

4. The endoscope video processing system of claim 2, wherein the first weight is a constant value while the second weight has a value depending on surrounding luminance.

5. The endoscope video processing system of claim 1, wherein the average luminance value is calculated using Gaussian weights.

6. The endoscope video processing system of claim 2, wherein a center point of the sigmoid function approximates 240/(1+second weight), wherein said image sensor comprises a CCD sensor.

7. The endoscope video processing system of claim 2, wherein a center point of the sigmoid function approximates 255/(1+second weight), wherein said image sensor comprises a CMOS sensor.

8. The endoscope video processing system of claim 2, wherein a center point of the sigmoid function approximates 100/(1+second weight), wherein said image sensor comprises a CMOS sensor.

9. The endoscope video processing system of claim 2, wherein a center point of the sigmoid function decreases as the second weight increases and said center point increases as the second weight decreases.

10. The endoscope video processing system of claim 1, wherein the customizable digital gain meets a plurality of conditions, said plurality of conditions including at least one of:
    a value of said digital gain approaches 1.0 as a brightness of a region of the image frame nears maximal value;
    said digital gain has an upper limit of 5.0 in a region of the image frame that, relative to all other regions in said image frame, is darkest; or
    said digital gain transitions from a region of a first brightness to a region of a second brightness, wherein the first brightness is greater than the second brightness, in a smooth manner.

11. A method comprising:
    generating a video data signal and corresponding image frame with a viewing element of an endoscope, wherein the viewing element includes an image sensor, and, implementing the following using a controller of the endoscope:
    attenuating a luminance (Y) component of the video data signal of the viewing element to generate an attenuated signal, wherein the attenuation factor meets a condition such that a summation of a first weight $K_1$ and a second weight $K_2$ approximates a value equal to or less than 5.0;
    applying a Gaussian function to luminance levels of a plurality of pixels neighboring a given pixel of the attenuated signal to generate an average luminance signal Gaussian(Y);
    applying a sigmoid function to the average luminance signal to generate a modified signal sigmoid(Gaussian (Y)); and
    applying a digital gain to the attenuated signal, wherein the digital gain is determined by applying weights to the modified signal sigmoid (Gaussian(Y)), for controlling blooming in a plurality of regions of the image frame of the video data signal generated by the viewing element of the endoscope.

12. The method of claim 11, wherein the weights comprises a first weight $K_1$ and a second weight $K_2$, wherein $K_1$ is a constant value and $K_2$ has a value depending on surrounding luminance.

13. The method of claim 12, wherein a center point of the sigmoid function approximates 240/(1+second weight $K_2$), wherein said image sensor comprises a CCD sensor.

14. The method of claim 12, wherein a center point of the sigmoid function approximates 255/(1+second weight $K_2$), wherein said image sensor comprises a CMOS sensor.

15. The method of claim 12, wherein a center point of the sigmoid function approximates 100/(1+second weight $K_2$), wherein said image sensor comprises a CMOS sensor.

16. The method of claim 12, wherein a center point of the sigmoid function decreases as the second weight $K_2$ increases and said center point increases as the second weight $K_2$ decreases.

17. The method of claim 11, wherein the value of said digital gain approaches 1.0 as brightness of a region of the image frame nears maximum value.

18. The method of claim 11, wherein the value of said digital gain has an upper limit of 5.0 in a region of the image frame that, relative to all other regions in an image frame, is the darkest.

19. The method of claim 11, wherein said digital gain transitions from a region of a first brightness to a region of a second brightness, wherein the first brightness is greater than the second brightness, in a smooth manner.

\* \* \* \* \*